United States Patent
Rockweiler et al.

(10) Patent No.: US 10,449,367 B2
(45) Date of Patent: Oct. 22, 2019

(54) CARDIAC ANODAL ELECTROSTIMULATION DETECTION

(71) Applicant: Cardiac Pacemakers, Inc., St. Paul, MN (US)

(72) Inventors: Holly Rockweiler, San Francisco, CA (US); Shibaji Shome, Arden Hills, MN (US); Aaron R. McCabe, Edina, MN (US); Rachel A. Taylor, Bogart, GA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 460 days.

(21) Appl. No.: 14/742,287

(22) Filed: Jun. 17, 2015

(65) Prior Publication Data

US 2015/0283388 A1  Oct. 8, 2015

Related U.S. Application Data

(63) Continuation of application No. 13/301,162, filed on Nov. 21, 2011, now Pat. No. 9,061,158.

(60) Provisional application No. 61/416,506, filed on Nov. 23, 2010.

(51) Int. Cl.
*A61N 1/37* (2006.01)
*A61N 1/05* (2006.01)
*A61B 7/04* (2006.01)

(52) U.S. Cl.
CPC ........... *A61N 1/3712* (2013.01); *A61N 1/056* (2013.01); *A61N 1/3702* (2013.01); *A61B 7/04* (2013.01)

(58) Field of Classification Search
CPC .... A61N 1/3627; A61N 1/3712; A61N 1/056; A61N 1/3684; A61B 5/0422; A61B 5/6858

USPC .......................................................... 607/18
See application file for complete search history.

(56) References Cited

U.S. PATENT DOCUMENTS

| | | | |
|---|---|---|---|
| 6,687,545 | B1 | 2/2004 | Lu |
| 6,937,901 | B2 | 8/2005 | Zhu et al. |
| 6,978,178 | B2 | 12/2005 | Sommer et al. |
| 7,236,825 | B2 | 6/2007 | Wang |
| 7,373,202 | B1 | 5/2008 | Kroll |
| 7,711,424 | B2 | 5/2010 | Meyer et al. |
| 8,233,979 | B1 * | 7/2012 | Shelchuk ............. A61B 5/0031 600/374 |

(Continued)

FOREIGN PATENT DOCUMENTS

| | | |
|---|---|---|
| JP | 2009531131 A | 9/2009 |
| JP | 2013543787 A | 12/2013 |

(Continued)

OTHER PUBLICATIONS

"U.S. Appl. No. 13/301,162, Final Office Action dated Jan. 2, 2015", 8 pgs.

(Continued)

*Primary Examiner* — Catherine M Voorhees
*Assistant Examiner* — Natasha Patel
(74) *Attorney, Agent, or Firm* — Schwegman Lundberg & Woessner, P.A.

(57) ABSTRACT

Cardiac anodal electrostimulation detection systems and methods are described, such as for distinguishing between cathodal-only capture and at least partially anodal capture (e.g., combined anodal and cathodal capture, or between two anodes of which only one captures nearby cardiac tissue, etc.).

20 Claims, 17 Drawing Sheets

(56) References Cited

U.S. PATENT DOCUMENTS

| | | | |
|---|---|---|---|
| 9,061,158 B2 | 6/2015 | Rockweiler et al. | |
| 2003/0204214 A1* | 10/2003 | Ferek-Patric | A61N 1/36185 607/27 |
| 2007/0276446 A1 | 11/2007 | Spinelli et al. | |
| 2009/0030470 A1* | 1/2009 | Holmstrom | A61N 1/371 607/27 |
| 2009/0043352 A1* | 2/2009 | Brooke | A61N 1/36185 607/28 |
| 2009/0088827 A1* | 4/2009 | Tockman | A61N 1/056 607/123 |
| 2010/0121396 A1* | 5/2010 | Gill | A61B 5/6846 607/17 |
| 2010/0262204 A1 | 10/2010 | Mccabe et al. | |
| 2012/0130442 A1 | 5/2012 | Rockweiler et al. | |
| 2013/0184777 A1* | 7/2013 | Hellman | A61B 5/0452 607/28 |
| 2015/0306410 A1* | 10/2015 | Marshall | A61N 1/05 607/4 |

FOREIGN PATENT DOCUMENTS

| | | |
|---|---|---|
| WO | WO-0156651 A1 | 8/2001 |
| WO | WO-2007086782 | 8/2007 |
| WO | WO-2007086782 A1 | 8/2007 |
| WO | WO-2008130293 | 10/2008 |
| WO | WO-2008130293 A1 | 10/2008 |
| WO | WO-2012071331 | 5/2012 |

OTHER PUBLICATIONS

"U.S. Appl. No. 13/301,162, Non Final Office Action dated Jul. 17, 2014", 8 pgs.
"U.S. Appl. No. 13/301,162, Notice of Allowance dated Feb. 25, 2015", 7 pgs.
"U.S. Appl. No. 13/301,162, Response filed Feb. 10, 2015 to Final Office Action dated Jan. 2, 2015", 10 pgs.
"U.S. Appl. No. 13/301,162, Response filed Apr. 29, 2014 to Restriction Requirement dated Mar. 21, 2014", 9 pgs.
"U.S. Appl. No. 13/301,162, Response filed Sep. 25, 2014 to Non Final Office Action dated Jul. 17, 2014", 10 pgs.
"U.S. Appl. No. 13/301,162, Restriction Requirement dated Mar. 21, 2014", 9 pgs.
"International Application Serial No. PCT/US2011/061664, International Preliminary Report on Patentability dated Jun. 6, 2013", 7 pgs.
"International Application Serial No. PCT/US2011/061664, International Search Report dated May 24, 2012", 4 pgs.
"International Application Serial No. PCT/US2011/061664, Written Opinion dated May 24, 2012", 5 pgs.
"Japanese Application Serial No. 2013-540994, Office Action dated Apr. 1, 2014", With English Translation, 8 pgs.
"Japanese Application Serial No. 2013-540994, Response filed Jun. 13, 2014 to Non Final Office Action dated Apr. 1, 2014", With English Claims, 12.
Alonso, C., "Electrocardiographic Predictive Factors of Long-Term Clinical Improvement with Multisite Biventricular Pacing in Advanced Heart Failure", The American Journal of Cardiology (US), vol. 84, No. 12, (Dec. 1999), 1417-1421.
Auricchio, A., "Effect of Pacing Chamber and Atrioventricular Delay on Acute Systolic Function of Paced Patients With Congestive Heart Failure", Circulation, 99(23), (Jun. 15, 1999), 2993-3001.
Barold, S. S., et al., "Electrocardiographic Follow-Up of Biventricular Pacemakers", Ann Noninvasive Electrocardiol, 10(2), (2005), p. 231-55.
Blanc, J.J., et al., "Midterm Benefits of Left Univentricular Pacing in Patients With Congestive Heart Failure", Circulation, 109(14), (2004), p. 1741-4.
Bulava, Alan, et al., "Triple-Site Pacing in Patients with Biventricular Device—Incidence of the Phenomenon and Cardiac Resynchronization Benefit", Journal of Interventional Cardiac Electrophysiology, 10, (2004), 37-45.

Herweg, B., et al., "Anodel capture with second-generation biventricular cardioverter-defibrillator", Acta Cardiol, 58(5), (2003), p. 435-6.
Hummel, J. D., et al., "Augmentation of Cardiac Output by Anodal Pacing", [Abstract] Circulation, 90(No. 4, Part 2), (Oct. 1994), p. I-69.
Irwin, M. E., et al., "Electrocardiography of cardiac resynchronization therapy: Phenomenon of left cathode and right anodal capture", [Abstract] Heart Rhythm, 1 (May Suppl.), (2004), p. S276.
Mehra, R., et al., "Vulnerability of the Mildly Ischemic Ventricle to Cathodal, Anodal, and Bipolar Stimulation", Circ Res, 41(2), (1977), p. 159-66.
Meine, M., et al., "Anodel stimulation in three chamber implantable cardioverter/defibrillator (ICD) devices with unipolar left ventricular pacing leads: Is it a problem for VV sequential pacing?", [Abstract] Europace, 6 (Suppl. 1), (2004), p. 183.
Mounsey, J. P, et al., "Anodel capture, cathodal capture, and left ventricular cardiac excitation", J Cardiovasc Electrophysiol., 20(6), (Jun. 2009), 650-2.
Nelson, G., et al., "Left ventricular or biventricular pacing improves cardiac function at diminished energy cost in patients with dilated cardiomyopathy and left bundle-branch block", Circulation, 102(25), (Dec. 19, 2000), 3053-9.
Sauer, W. H., et al., "Increasing Left Ventricular Pacing Output Decreases Interventricular Conduction Time in Patients with Biventricular Pacing Systems", Pacing and Clinical Electrophysiology, 29(6):, (2006), p. 569-573.
Steinhaus, D., et al., "Right ventricular anodel capture in biventricular stimulation for heart failure: a look at multiple lead models", [Abstract] J Am Coll Cardiol, 39 (Suppl. A), (2002), p. 107A.
Steinhaus, David M., et al., "Anodal Stimulation: A Potential Concern with Biventricular Pacing?", PACE, vol. 24, 553, (Apr. 2001), 3 pgs.
Tamborero, David, et al., "Anodel capture in cardiac resynchronization therapy implications for device programming", Pacing Clin Electrophysiol., 29(9), (Sep. 2006), 940-5.
Thakral, A, et al., "Effects of anodel vs. cathodal pacing on the mechanical performance of the isolated rabbit heart", J. Appl Physiol., 89(3), (Sep. 2000), 1159-64.
Thibault, B., et al., "Anodel right ventricular capture during left ventricular stimulation in CRT-implantable cardioverter defibrillators", Pacing Clin Electrophysiol, 28(7), (2005), p. 613-9.
Van Gelder, B. M., et al., "Effect of optimizing the VV interval on left ventricular contractility in cardiac resynchronization therapy", Am J Cardiol., 93(12), (Jun. 15, 2004), 1500-3.
Van Gelder, B. M., et al., "Right ventricular anodel capture during left ventricular stimulation in CRT-implantable cardioverter defibrillators (ICD)", [Author Reply] Pacing Clin Electrophysiol, 29(3), (2006), p. 337-8.
Van Gelder, B. M., et al., "The Effect of Anodal Stimulation on V-V Timing at Varying V-V Intervals", Pacing Clin Electrophysiol, 28(8), (2005), p. 771-6.
Van Gelder, B. M., et al., "Triple-Site Ventricular Pacing in a Biventricular Pacing System", Pacing Clin Electrophysiol, 24(7):, (2001), p. 1165-7.
Van Gelder, L. M., et al., "Changes in morphology of the paced QRS complex related to pacemaker output", Pacing Clin Electrophysiol, 12(10), (1989), p. 1640-9.
Vanderheyden, M., et al., "Tailored echocardiographic interventricular delay programming further optimizes left ventricular performance after cardiac resynchronization therapy", Heart Rhythm, 2(10), (Oct. 2005), 1066-72.
"European Application Serial No. 11791169.3, Communication Pursuant to Article 94(3) EPC dated Nov. 15, 2016", 4 pgs.
"European Application Serial No. 11791169.3, Summons to Attend Oral Proceedings mailed Nov. 29, 2017", 8 pgs.
"European Application Serial No. 11791169.3, Written Submissions filed Apr. 11, 2018 to Summons to Attend Oral Proceedings mailed Nov. 29, 2017", 16 pgs.
"European Application Serial No. 11791169.3, Response filed Apr. 6, 2017 to Communication Pursuant to Article 94(3) EPC dated Nov. 15, 2016", 12 pgs.

\* cited by examiner

CARDIAC ANODAL ELECTROSTIMULATION DETECTION

CROSS-REFERENCE TO RELATED APPLICATION

This application is a continuation of U.S. application Ser. No. 13/301,162, filed Nov. 21, 2011, which claims the benefit of U.S. Provisional Application No. 61/416,506, filed on Nov. 23, 2010, under 35 U.S.C. § 119(e), each of which is hereby incorporated by reference in its entirety.

BACKGROUND

Electrostimulation can be delivered to a heart, such as to trigger or to spatially coordinate a responsive cardiac depolarization and accompanying heart contraction. An implantable or other ambulatory cardiac function management device, such as a pacer, a cardioverter, a defibrillator, a cardiac contractility modulation (CCM) or a cardiac resynchronization therapy (CRT) device can be configured to include capability for monitoring cardiovascular function or for generating or providing such stimulation to the heart, such as for triggering or spatially coordinating responsive heart contractions. Such electrostimulations can be delivered via two or more electrodes. For example, such electrodes can include one or more electrodes that can be located at or near the distal end of one or more implantable leadwires, which can be connected to an implantable cardiac function management device. Such electrodes can also include one or more electrodes located at the implantable cardiac function management device.

Electrostimulation can be either cathodal or anodal, or a combination of anodal and cathodal. In cathodal stimulation, a more negative electrode (e.g., in an arrangement of electrodes) "captures" contractile cardiac tissue to trigger the resulting cardiac depolarization and accompanying heart contraction. In anodal stimulation, a more positive electrode (e.g., in an arrangement of electrodes) triggers the resulting cardiac depolarization and accompanying heart contraction. Various factors can influence whether anodal or cathodal stimulation occurs. For example, relative electrode size of an anode vs. a cathode can determine whether anodal, cathodal, or a combination of anodal and cathodal stimulation occurs. An electrode having a smaller surface area can have a greater current density through nearby tissue than a larger electrode. Greater current density can lower the threshold amount of energy needed to evoke a resulting cardiac depolarization and accompanying heart contraction.

The threshold amount of energy needed to evoke a resulting cardiac depolarization and accompanying heart contraction can differ for anodal stimulation vs. cathodal stimulation. Because cathodal stimulation typically needs less energy to accomplish the desired result of capturing cardiac tissue to evoke a resulting heart contraction, it can be preferred over anodal stimulation. This is because the useful life of an implantable device can depend on how quickly its battery is depleted. If a desired stimulation can be accomplished using less energy, that can prolong the useful life of an implanted device before the device is explanted. Such explantation can expose a subject to increased health care cost and the potential risk of infection that is associated with any invasive surgical procedure. Because of these and other potential differences in anodal vs. cathodal stimulation, it can be useful to detect whether a particular stimulation is anodal in nature. A description of anodal capture, cathodal capture, and left ventricular cardiac excitation is provided in J. Paul Mounsey and Stephen B Knisley, "ANODAL CAPTURE, CATHODAL CAPTURE, AND LEFT VENTRICULAR CARDIAC EXCITATION," Journal of Cardiovascular Electrophysiology, Vol. 20, No. 6, June 2009, pages 650-652, which is incorporated herein by reference in its entirety.

In Lu U.S. Pat. No. 6,687,545, anodal stimulation is detected by the absence of a delay between a bipolar stimulation pulse and an evoked response sensed at an electrode functioning as the anode during stimulation.

In Bjorling WO 2008/130293, anodal stimulation is detected using a paced depolarization integral (PDI) initialization test. For a 0.5 ms pacing pulsewidth, pacing amplitude is varied, and a portion of the evoked cardiac electrogram is integrated to provide a PDI. For cathodal stimulation, PDI vs. amplitude exhibits two distinct plateaus, by contrast, for anodal stimulation, three distinct plateaus are exhibited.

Also in Bjorling WO 2008/130293, anodal stimulation is detected by measuring a temporal distance between an applied stimulation pulse and a morphological feature—the morphological feature being the minimum value of the evoked response signal. Bjorling WO 2008/130293 notes that the temporal distance is shorter for anodal capture than cathodal capture, when the intracardiac electrogram (IEGM) is measured between a left ventricular (LV) ring electrode and a case electrode at the case housing the electronics of the implantable device, and that the temporal distance is longer for anodal capture than cathodal capture when the IEGM is measured between a LV tip electrode and the case electrode.

Overview

Cardiac anodal electrostimulation detection systems and methods are described, such as for distinguishing between cathodal-only capture and at least partially anodal capture (e.g., combined anodal and cathodal capture, or between two anodes of which only one captures nearby cardiac tissue, etc.).

Example 1 can include subject matter (such as an apparatus, such as an implantable cardiac function management device, a method, a means for performing acts, or a machine-readable medium including instructions that, when performed by the machine, cause the machine to perform acts, etc.) that can include: an electrostimulation energy delivery circuit, configured to issue electrostimulations for delivery using first and second pacing electrodes; an evoked response (ER) cardiac signal sensing circuit, configured to sense ER signals of the subject, in response to respective electrostimulations, using first and second sensing electrodes; and a processor circuit, coupled to the ER cardiac signal sensing circuit and the electrostimulation energy delivery circuit, wherein in an operating mode of the device, the processor circuit is configured to adjust electrostimulation energy while monitoring a characteristic of the ER signal, and is configured to declare a change in capture, which is capable of distinguishing a change in at least partially anodal capture, when the characteristic of the ER signal meets at least one criteria.

In Example 2, the subject matter of Example 1 can optionally be configured such that at least one of the first and second pacing electrodes is separate from the first and second sensing electrodes.

In Example 3, the subject matter of one or any combination of Examples 1-2 can optionally be configured such that the characteristic includes a time delay between an electrostimulation and an ER signal feature responsive to the electrostimulation.

In Example 4, the subject matter of one or any combination of Examples 1-3 can optionally be configured such that the at least one criteria is selected to identify a change in the time delay that corresponds to one of: a shift from cathodal-only capture to at least partially anodal capture; or a shift from at least partially anodal capture to cathodal-only capture.

In Example 5, the subject matter of one or any combination of Examples 1-4 can optionally be configured such that the first pacing electrode includes a first right ventricular (RV) electrode and the second pacing electrode includes a first left ventricular (LV) electrode, and wherein the first sensing electrode includes one of a second RV electrode that is separate from the first RV electrode or a second LV electrode that is separate from the first LV electrode, and wherein the second sensing electrode includes at least one of an extracardiac electrode or an intracardiac shock electrode.

In Example 6, the subject matter of one or any combination of Examples 1-4 can optionally be configured such that the first pacing electrode includes a first left ventricular (LV) electrode and the second pacing electrode includes a second LV electrode, and wherein the first sensing electrode includes a third LV electrode that is separate from the first and second LV electrodes and the second sensing electrode includes at least one of an extracardiac electrode or an intracardiac shock electrode.

In Example 7, the subject matter of one or any combination of Examples 1-6 can optionally be configured such that the characteristic includes a time delay between (1) the electrostimulation or a first ER signal feature responsive to the electrostimulation, and (2) a later second ER signal feature responsive to the electrostimulation, wherein the second ER signal feature includes a first local minimum of the ER signal.

In Example 8, the subject matter of one or any combination of Examples 1-7 can optionally be configured such that the at least one criteria is selected to identify a change in the time delay that corresponds to one of: a shift from cathodal-only capture to at least partially anodal capture; or a shift from at least partially anodal capture to cathodal-only capture.

In Example 9, the subject matter of one or any combination of Examples 1-8 can optionally be configured such that the first pacing electrode includes a first right ventricular (RV) electrode and the second pacing electrode includes a first left ventricular (LV) electrode, and wherein the first sensing electrode includes one of a second RV electrode that is separate from the first RV electrode or a second LV electrode that is separate from the first LV electrode, and wherein the second sensing electrode includes at least one of an extracardiac electrode or an intracardiac shock electrode.

In Example 10, the subject matter of one or any combination of Examples 1-9 can optionally be configured such that the characteristic includes a time delay between (1) the electrostimulation or a first ER signal feature responsive to the electrostimulation, and (2) a later second ER signal feature responsive to the electrostimulation, wherein the second ER signal feature includes an absolute minimum of the ER signal.

In Example 11, the subject matter of one or any combination of Examples 1-10 can optionally be configured such that the at least one criteria is selected to identify a change in the time delay that corresponds to one of: a shift from cathodal-only capture to at least partially anodal capture; or a shift from at least partially anodal capture to no anodal capture.

In Example 12, the subject matter of one or any combination of Examples 1-11 can optionally be configured such that the first pacing electrode includes a first right ventricular (RV) electrode and the second pacing electrode includes a first left ventricular (LV) electrode, and wherein the first sensing electrode includes one of a second RV electrode that is separate from the first RV electrode or a second LV electrode that is separate from the first LV electrode, and wherein the second sensing electrode includes at least one of an extracardiac electrode or an intracardiac shock electrode.

In Example 13, the subject matter of one or any combination of Examples 1-12 can optionally be configured such that the characteristic includes a slope of the ER signal taken between first and second ER signal features responsive to the electrostimulation, wherein the first ER signal feature includes a minimum of the ER signal and wherein the second ER signal feature includes a next maximum of the ER signal.

In Example 14, the subject matter of one or any combination of Examples 1-13 can optionally be configured such that the at least one criteria is selected to identify a change in the slope that corresponds to one of: a shift from cathodal-only capture to at least partially anodal capture; or a shift from at least partially anodal capture to cathodal-only capture.

In Example 15, the subject matter of one or any combination of Examples 1-14 can optionally be configured such that the first pacing electrode includes a first right ventricular (RV) electrode and the second pacing electrode includes a first left ventricular (LV) electrode, and wherein the first sensing electrode includes one of a second RV electrode that is separate from the first RV electrode or a second LV electrode that is separate from the first LV electrode, and wherein the second sensing electrode includes at least one of an extracardiac electrode or an intracardiac shock electrode.

In Example 16, the subject matter of one or any combination of Examples 1-15 can optionally be configured such that the first pacing electrode includes a first left ventricular (LV) electrode and the second pacing electrode includes a second LV electrode, and wherein the first sensing electrode includes a third LV electrode that is separate from the first and second LV electrodes and the second sensing electrode includes at least one of an extracardiac electrode or an intracardiac shock electrode.

In Example 17, the subject matter of one or any combination of Examples 1-16 can optionally comprise at least one of the first pacing electrode, the second pacing electrode, the first sensing electrode, or the second sensing electrode.

In Example 18, the subject matter of one or any combination of Examples 1-17 can optionally be configured such that the characteristic includes an indication of a width of an S-wave of the ER signal.

In Example 19, the subject matter of one or any combination of Examples 1-18 can optionally include a heart-sound sensing circuit configured to sense a heart-sound signal representative of mechanical activation of the heart of the subject. The processor circuit can optionally be configured to monitor a parameter of at least one heart-sound detected in the heart-sound signal, detect at least partial anodal capture in response to adjusting the electrostimulation energy, adopt the electrostimulation adjustment when the monitored heart-sound parameter indicates that hemodynamic performance of the patient is maintained or improved, and reject the electrostimulation adjustment when the monitored heart-sound parameter indicates a decrease in hemodynamic performance of the subject.

In Example 20, the subject matter of one or any combination of Examples 1-19 can optionally include at least one of the first pacing electrode, the second pacing electrode, the first sensing electrode, or the second sensing electrode.

In Example 21, the subject matter of one or any combination of Examples 1-20 can optionally be configured such that the processor circuit is configured to direct the electrostimulation energy delivery circuit to use a unipolar pacing configuration for generating a reference template to which a candidate electrode configuration sharing the same cathode as the unipolar pacing configuration is compared to determine whether the characteristic of the ER signal meets the at least one criteria.

In Example 22, the subject matter of one or any combination of Examples 1-21 can optionally include the ER sensing circuit including a heart-sound sensing circuit. The heart-sound sensing circuit can optionally sense the ER signal as a heart-sound signal representative of mechanical activation of the heart of the subject.

In Example 23, the subject matter of one or any combination of Examples 1-22 can optionally include the processor circuit configured to monitor a characteristic of the ER signal that includes a time delay between an electrostimulation and a feature of a heart-sound responsive to the electrostimulation.

In Example 24, the subject matter of one or any combination of Examples 1-23 can optionally include the processor circuit configured to monitor a characteristic of the ER signal that includes a time delay between an electrostimulation and at least one of an onset of the heart-sound in the heart-sound signal and a peak of the heart-sound in the heart-sound signal.

In Example 25, the subject matter of one or any combination of Examples 1-24 can optionally include the processor circuit configured to declare a change in capture according to at least one criterion that includes at least one of a shift from cathodal-only capture to at least partially anodal capture, or a shift from at least partially anodal capture to cathodal-only capture.

In Example 26, the subject matter of one or any combination of Examples 1-25 can optionally be configured so that the first pacing electrode includes a first left ventricular (LV) electrode and the second pacing electrode includes a second LV electrode.

In Example 27, the subject matter of one or any combination of Examples 1-26 can optionally be configured so that the first pacing electrode includes an LV electrode and the second pacing electrode includes a right ventricular (RV) electrode.

Example 28 can include, or can be combined with the subject matter of one or any combination of Examples 1-27 to optionally include, subject matter (such as an apparatus, such as an implantable cardiac function management device, a method, a means for performing acts, or a machine-readable medium including instructions that, when performed by the machine, cause the machine to perform acts) that can comprise: an electrostimulation energy delivery circuit, configured to issue electrostimulations for delivery using first and second pacing electrodes; an evoked response (ER) cardiac signal sensing circuit, configured to sense ER signals of the subject, in response to respective electrostimulations, using first and second sensing electrodes, wherein the first pacing electrode is separate from the first and second sensing electrodes; a processor circuit, coupled to the ER cardiac signal sensing circuit and the electrostimulation energy delivery circuit, wherein in an automatic threshold mode of the device, the processor circuit is configured to incrementally increase or incrementally decrease electrostimulation energy while monitoring a characteristic of the ER signal, and is configured to declare a change in capture, which is capable of distinguishing a change in at least partially anodal capture, when the characteristic of the ER signal meets at least one criteria; wherein the characteristic includes a slope of the ER signal taken between first and second ER signal features responsive to the electrostimulation, wherein the first ER signal feature includes a first local minimum of the ER signal and wherein the second ER signal feature includes a next local maximum of the ER signal; wherein the at least one criteria is selected to identify a change in the slope such that at least one of: a specified decrease in the slope corresponds to a shift from cathodal-only capture to at least partially anodal capture; or a specified increase in the slope corresponds to a shift from at least partially anodal capture to cathodal-only capture; and wherein the first pacing electrode includes a first right ventricular (RV) electrode as an anode and the second pacing electrode includes a first left ventricular (LV) electrode as a cathode, and wherein the first sensing electrode includes a second LV electrode that is separate from the first LV electrode and wherein the second sensing electrode includes at least one of an extracardiac electrode or an intracardiac shock electrode.

Example 29 can include, or can be combined with the subject matter of one or any combination of Examples 1-28 to optionally include, subject matter (such as an apparatus, such as an implantable cardiac function management device, a method, a means for performing acts, or a machine-readable medium including instructions that, when performed by the machine, cause the machine to perform acts) that can comprise: an electrostimulation energy delivery circuit, configured to issue electrostimulations for delivery using first and second pacing electrodes; an evoked response (ER) cardiac signal sensing circuit, configured to sense ER signals of the subject, in response to respective electrostimulations, using first and second sensing electrodes, wherein the first pacing electrode is separate from the first and second sensing electrodes; a processor circuit, coupled to the ER cardiac signal sensing circuit and the electrostimulation energy delivery circuit, wherein in an automatic threshold mode of the device, the processor circuit is configured to incrementally increase or incrementally decrease electrostimulation energy while monitoring a characteristic of the ER signal, and is configured to declare a change in capture, which is capable of distinguishing a change in at least partially anodal capture, when the characteristic of the ER signal meets at least one criteria; wherein the characteristic includes a slope of the ER signal taken between first and second ER signal features responsive to the electrostimulation, wherein the first ER signal feature includes a first local minimum of the ER signal and wherein the second ER signal feature includes a next local maximum of the ER signal; wherein the at least one criteria is selected to identify a change in the slope such that at least one of: a specified increase in the slope corresponds to a shift from cathodal only capture to at least partially anodal capture; or a specified decrease in the slope corresponds to a shift from at least partially anodal capture to cathodal-only capture; and wherein the first pacing electrode includes a first left ventricular (LV) electrode as an anode and the second pacing electrode includes a second LV electrode as a cathode, and wherein the first sensing electrode includes a third LV electrode that is separate from the first and second LV electrodes, and wherein the third LV electrode is closer to the first LV electrode than to the second LV electrode, and wherein the second sensing electrode includes at least one of an extracardiac electrode or an intracardiac shock electrode.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
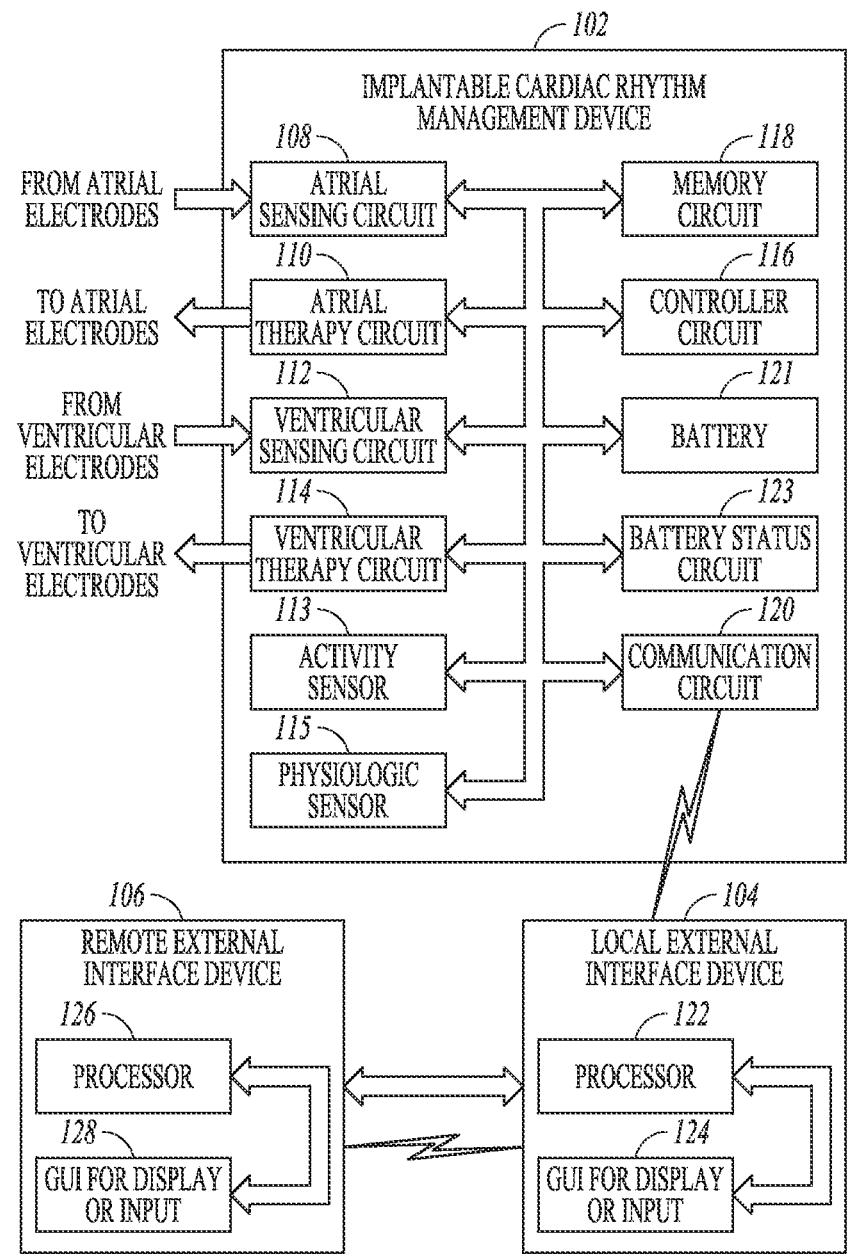
FIG. 1 shows an example of portions of a cardiac function management system and an environment in which it is used.

FIG. 1 shows an example of portions of a cardiac function management system 100 and an environment in which it is used. In an example, the system 100 can include an ambulatory medical device, such as an external (e.g., wearable) medical device or an implantable cardiac rhythm or function management device 102 for monitoring physiological function or delivering therapy, a local external interface device 104, and an optional remote external interface device 106.

In an example, the implantable device 102 can include an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 121, a battery status circuit 123, an activity sensor 113 configured to sense a physical activity signal of a patient or other subject, and a physiologic sensor 115 configured to sense a physiologic signal, different from the physical activity signal, of the subject.

In an example, the atrial sensing circuit 108 can be coupled to electrodes, such as an intra-atrial electrode or any other electrode that permits sensing of an intrinsic atrial cardiac signal including atrial depolarization information. The atrial therapy circuit 110 can similarly be coupled to these or other electrodes, such as for delivering pacing, cardiac resynchronization therapy (CRT), cardiac contractility modulation (CCM) therapy, defibrillation/cardioversion shocks, or other energy pulses to one or both atria. In an example, the atrial sensing circuit 108 or the atrial therapy circuit 110 can be multiplexed or replicated, such as to interface with both a right atrium and a left atrium.

In an example, the ventricular sensing circuit 112 can be coupled to electrodes, such as an intra-ventricular electrode or any other electrode that permits sensing of an intrinsic ventricular cardiac signal including ventricular depolarization information. The ventricular therapy circuit 114 can similarly be coupled to these or other electrodes, such as for delivering pacing, cardiac resynchronization therapy (CRT), cardiac contractility modulation (CCM) therapy, defibrillation/cardioversion shocks, or other energy pulses to one or both ventricles. In an example, the ventricular sensing circuit 112 or the ventricular therapy circuit 114 can be multiplexed or replicated, such as to interface with both a right ventricle and a left ventricle.

In an example, the activity sensor 113 can include a single or multiple axis accelerometer, such as to sense an acceleration of the subject that is indicative of physical activity of the subject. The activity sensor 113 can also include a sensor interface circuit, configured to process the acceleration signal and provide a resulting physical activity signal. In an example, the physical activity signal can be indicative of a physical exertion of the subject. In an example, the activity sensor 113 can also be used for one or more other purposes, such as to sense the subject's posture, heart-sounds, or other information available from an acceleration signal.

In an example, the physiologic sensor 115 can include a respiration sensor, such as an impedance or other sensor, which can include electrodes configured to deliver a test energy, such as to the subject's thorax, and to sense a responsive voltage signal, such as indicative of the thoracic impedance, and which can be filtered to provide information about respiration (e.g., minute ventilation), heart contraction, or thoracic fluid accumulation.

A controller circuit 116 can be coupled to the atrial sensing circuit 108 and the ventricular sensing circuit 112, such as to receive information from the sensed cardiac signals. The controller circuit 116 can also be coupled to the activity sensor 113 to receive information about the subject's physical activity or exertion level. The controller circuit 116 can also be coupled to the physiologic sensor 115, such as to receive other physiologic information. In an example, such other physiologic information can include cardiac contraction signal, such as to provide information about the subject's heart rate or interval, stroke volume, or other information available from the cardiac contraction signal. In an example, the other physiologic information can include a respiration signal, such as to provide information about the subject's breathing rate or interval, tidal volume, or other information available from the respiration signal. In an example, the controller circuit 116 can include a signal processor circuit, such as a digital signal processor (DSP) circuit.

In an example, the controller circuit 116 can be coupled to the atrial therapy circuit 110 and the ventricular therapy circuit 114 such as to provide control or triggering signals to trigger timed delivery of the therapy pulses. In an example, the controller circuit 116 can be configured to provide control to help permit the therapy to be effectively delivered, such as in combination with one or more other therapies (e.g., bradycardia pacing, antitachyarrhythmia pacing (ATP), cardiac contractility modulation (CCM) therapy, cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.). In an example, this can include providing dedicated modules within the controller circuit 116, or providing executable, interpretable, or otherwise performable code on a tangible machine-readable medium to configure the controller circuit 116.

A memory circuit 118 can be coupled to the controller circuit 116, such as to store control parameter values, physiological data, performable code or instructions, or other information. A communication circuit 120 can be coupled to the controller circuit 116 such as to permit radiofrequency (RF) or other wireless communication with an external device, such as the local external interface device 104 or the remote external interface device 106.

In an example, the battery 121 can include one or more batteries to provide power for the implantable device 102. In an example, the battery 121 can be rechargeable, such as by wireless transcutaneous power transmission from an external device to the implantable device 102. The battery status circuit 123 can be communicatively coupled to each of the battery 121 and the controller circuit 116, such as to determine battery status information, for example, indicative of how much energy remains stored in the battery 121. The controller circuit 116 can be configured to alter operation of the implantable device 102, such as based at least in part on the battery status information.

In an example, the local external interface device 104 can include a processor 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 can include a processor 126 and a graphic user interface (GUI) 128 or like device for displaying information or receiving user input as well as a communication circuit, such as to permit wired or wireless communication with the local external interface device 104 over the communications or computer network.

Because the system 100 includes processing capability in the ambulatory or implantable device 102 (e.g., provided by the controller circuit 116), the local external interface device 104 (e.g., provided by the processor 122), and the remote external interface device 106 (e.g., provided by the processor 126), various functions or methods discussed in this document can be implemented at any of such locations, or tasks of such functions or methods can be distributed between two or more of such locations.

Figure 2:
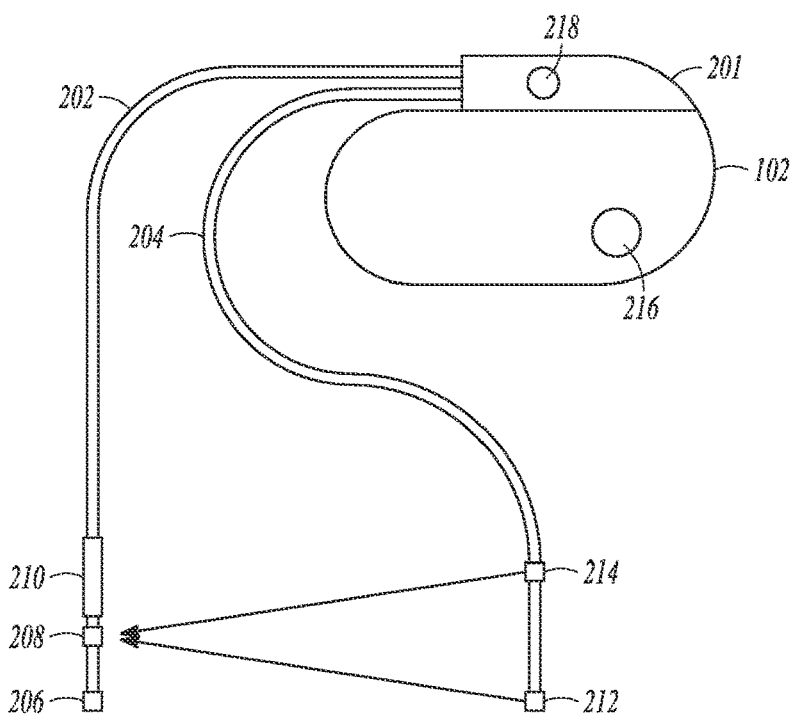
FIG. 2 shows an example of the implantable device connected at a header portion to a right ventricular (RV) intravascular leadwire and a left ventricular/coronary sinus (LV/CS) intravascular leadwire, such as for use in an "extended bipolar" pacing configuration.

FIG. 2 shows an example of the implantable device 102 connected at a header portion 201 to a right ventricular (RV) intravascular leadwire 202 and a left ventricular/coronary sinus (LV/CS) intravascular leadwire 204. In an example, the RV leadwire 202 can include one or more of an RV tip electrode 206, an RV ring electrode 208, an RV coil electrode 210, or an RA/superior vena cava (SVC) coil electrode. In an example, such electrodes can be separately addressable, for example, the RV ring electrode 208 can be separately addressable from the RV coil electrode 210, such as to provide a "dedicated bipolar" pacing or sensing electrode configuration using the RV ring electrode 208 and the RV tip electrode 206. In another example, the RV ring electrode 208 and the RV tip electrode 206 can be provided without the RV coil electrode 210 and the RA/SVC coil electrode. In an example, the LV/CS leadwire 204 can include one or more of an LV tip electrode 212 and LV ring electrode 214. In an example, the implantable device 102 can include an electrode, such as a "can" electrode 216 located on a conductive portion of a can-like hermetically-sealed housing of the electronics unit of the implantable device 102, or a "header" electrode 218 located on a conductive portion located on an insulating "header" extending from the housing of the electronics unit of the implantable device 102.

FIG. 2 illustrates an example of an "extended bipolar" pacing configuration, in which pacing pulses can be delivered between the LV ring electrode 214 and the RV ring electrode 208, or between the LV tip electrode 212 and the RV ring electrode 208. A potential consequence of such an extended bipolar pacing configuration can be cross-chamber anodal capture, such as which can occur when the anode electrode (e.g., RV ring electrode 208) has a small surface area, leading to a large current density near the anode. Such cross-chamber anodal capture can be unintentional or intentional.

When unintended, anodal capture can be difficult for a clinician to recognize in real-time, and can lead to a clinician inappropriately programming the implantable device 102. For example, during an automatic threshold test, a pacing energy can be lowered (e.g., by decreasing the pacing amplitude or pulsewidth) until loss of capture (LOC) is detected, such as by a change in morphology of an evoked-response (ER) intrinsic heart signal obtained during a time period after the pacing energy pulse is delivered. However, in an example in which the larger-energy pulses resulted in anodal capture at the RV ring electrode 208, a change in morphology of the evoked response signal can occur due to a loss of anodal capture at the RV ring electrode 208 (e.g., a shift from anodal and cathodal capture to cathodal-only capture), rather than due to a complete loss of capture. If a shift from anodal and cathodal capture to cathodal-only capture is inappropriately deemed a complete loss of capture by an automatic threshold measurement schema, then later pacing can be delivered in excess of a too-large determined pacing threshold voltage. This can shorten the useful life of the implantable device 102, such as where the implantable device 102 is powered by a non-rechargeable battery.

As another example of a possible consequence of unintended cross-chamber anodal capture, such as in the extended bipolar pacing configuration of FIG. 2, an unintended negation of interventricular delay can result. For example, a clinician may intend to use the extended bipolar electrode configuration of FIG. 2 to deliver individual RV and LV paces that are separated by a non-zero interventricular delay between such RV and LV paces. Such an interventricular delay can be referred to as a left ventricular (LV) offset. In an example, the clinician may want to issue an LV pace (e.g., between the LV ring electrode 214 and the RV ring electrode 208) slightly before issuing an RV pace (e.g., between the RV tip electrode 206 and the RV ring electrode 208). Such a non-zero time between the issued LV pace and the issued RV pace can be useful, such as where the left ventricular heart contraction is typically abnormally slower than or delayed from the right ventricular heart contraction, which can lead to inefficient blood pumping by the heart. By issuing an LV pace slightly before the RV pace, the left ventricular contraction can be coordinated with the right ventricular contraction, such that both the left and right ventricles contract more concurrently than would be the case without issuing such paces with a non-zero interventricular delay. However, if anodal capture occurs in the right ventricle (such as at the RV ring electrode 208) during an LV pace (e.g., between the LV ring electrode 214 and the RV ring electrode 208), then both right and left ventricles will be paced simultaneously, rather than with the intended non-zero delay between the LV pace pulse followed by the RV pace pulse (the later RV pace pulse may be ineffective, since the right ventricle is already contracting due to the anodal capture occurring with the earlier LV pace pulse). In such an example, the intended cardiac resynchronization providing spatial coordination between the right and left ventricles is absent, and the resulting slower contraction of the left ventricle than that of the right ventricle can result in compromised hemodynamics, such as less efficient pumping of blood than would be obtainable if the left and right ventricular contractions had been properly coordinated as intended. Moreover, it is believed that excessive right ventricular pacing can, over time, sometimes worsen a patient's congestive heart failure status. Delivery of an unintended RV pace pulse, such as that resulting in anodal capture or the later RV bipolar pace pulse rendered ineffective by the earlier anodal capture, can be undesirable.

By contrast, in certain examples, anodal capture can be intended. For example, in certain patients, zero delay between the LV pace pulse and the RV pace pulse can be desirable in spatially coordinating the left and right ventricles to contract together to promote more efficient pumping of blood. In an extended bipolar pacing example in which a pacing pulse is delivered between the RV ring electrode 208 and one of the LV ring electrode 214 and the LV tip electrode 212, if anodal capture occurs at the RV ring electrode 208 simultaneous with cathodal capture at one of the LV ring electrode 214 and the LV tip electrode 212, then bi-ventricular pacing can be provided via a single pace pulse that locally captures each ventricle, which can provide an energy-efficient way to perform bi-ventricular pacing or cardiac resynchronization. Similarly, in an extended bipolar pacing example in which a pacing pulse is delivered between the RV ring electrode 208 and both of the LV ring electrode 214 and the LV tip electrode 212, if anodal capture occurs at the RV ring electrode 208 simultaneous with cathodal capture at both of the LV ring electrode 214 and the LV tip electrode 212, then "triple site" bi-ventricular pacing can be provided via a single pace pulse that locally captures each ventricle at three different locations, which can resynchronize the heart by concurrently pacing at three different pacing sites, which can be advantageous for certain patients. In another example, "double site" pacing can be obtained, such as with anodal and cathodal capture occurring in the same heart chamber, for example, such as the RV.

Figure 3:
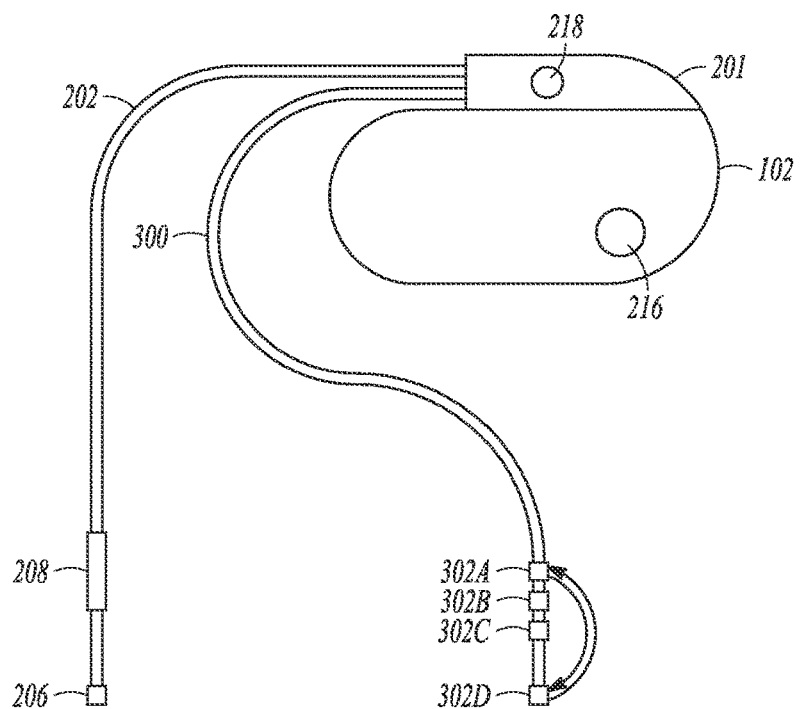
FIG. 3 shows an example of the implantable device connected at the header portion to a RV intravascular leadwire and a LV/CS intravascular leadwire, such as for use in a "wide bipolar" pacing configuration.

FIG. 3 shows an example of the implantable device 102 connected at the header portion 201 to a RV intravascular leadwire 202 and a LV/CS intravascular leadwire 300. In an example, the RV leadwire 202 can include one or more of an RV tip electrode 206, an RV ring electrode, an RV coil electrode 210, and an RA/superior vena cava (SVC) coil electrode. In an illustrative example that can include more than two electrodes, a quadripolar LV/CS leadwire 300 can include electrodes 302A-D, such as (e.g., listed proximally-to-distally) LV ring electrodes 302A, 302B, and 302C and an LV tip electrode 302D. In an example, the body of the quadripolar LV/CS leadwire 300 is thin enough to be inserted into the coronary sinus, such that one or more of the electrodes 302A-D can be positioned at desired locations in association with the left ventricle, such as within the great cardiac vein or near the LV lateral freewall, such as to provide CRT. The body of leadwire 300 can also include a distal portion having a shape-memory property, such as a tendency to spiral slightly, such as to impart a lateral mechanical bias force against one or more of the electrodes 302A-D, such as to position such one or more electrodes against a wall of the vasculature in which the distal portion of the leadwire 300 resides, such as to promote better capture of cardiac tissue from an electrostimulation or better intrinsic heart signal sensing.

In an example, the spacing between the electrodes 302A-D can be significant. For example, the spacing between the most proximal LV ring electrode 302A and the most distal LV tip electrode 302D can be about 30 millimeters or even 35 millimeters apart. FIG. 3 illustrates an example of a "wide bipolar" pacing configuration, such as in which pacing pulses can be delivered between the proximal LV ring electrode 302A and the distal LV tip electrode 302D. A potential consequence of such a wide bipolar pacing configuration can be within-chamber anodal capture, such as which can occur when the anode electrode (e.g., LV tip electrode 302D) has a small surface area, leading to a large current density near the anode. Such within-chamber anodal capture can be unintentional or intentional.

When unintended, concurrent within-chamber anodal capture (e.g., at LV tip electrode 302) and cathodal capture (e.g., at LV ring electrode 302A) can cause two intrinsic heart signal activation wavefronts propagating through the left ventricle. For a patient in which single-site pacing in the left ventricle (e.g., at the LV ring electrode 302A) is desired to better coordinate the right and left ventricular heart contractions, such dual-site anodal and cathodal capture may limit or reduce the benefit of the left-heart resynchronization, or may even result in less efficient blood pumping than would otherwise be obtained without such left-heart resynchronization. This illustrative example can be extended to pacing at more than two sites using anodal capture at one or more sites and cathodal capture at one or more sites.

By contrast, when intended, concurrent within-chamber anodal capture (e.g., at LV tip electrode 302) and cathodal capture (e.g., at LV ring electrode 302A) can cause two intrinsic heart signal activation wavefronts propagating through the left ventricle, which may benefit certain patients by providing improved spatial coordination of the left ventricle, or improved spatial coordination of the left ventricle with the right ventricle, which may result in improved blood pumping. Moreover, for such a patient that can so benefit, the dual-site within-chamber anodal and cathodal capture may be accomplished using less energy (e.g., that of a single pace pulse) than might otherwise be used (e.g., if two separate cathodal-capture pace pulses were delivered at the two different sites). This illustrative example can be extended to pacing at more than two sites using anodal capture at one or more sites and cathodal capture at one or more sites.

When unintended, anodal capture can also affect other functionality of the implantable device 102. In an example, the implantable device 102 can be configured to include an automatic vector selection (AVS) capability, such as described in U.S. patent application Ser. No. 12/724,729, entitled ANODAL STIMULATION DETECTION AND AVOIDANCE, which is assigned to Cardiac Pacemakers, Inc., and which is incorporated by reference herein in its entirety In an example, the AVS can automatically choose the "best" electrode configuration (sometimes referred to as a "vector"), such as for delivering an electrostimulation, for sensing an intrinsic electrical heart signal, or for both delivering an electrostimulation and sensing an intrinsic heart signal. One or more criteria can be applied to select the "best" electrode configuration for electrostimulation. In an example, threshold voltage for obtaining capture using a particular electrode configuration can be used as such a criterion for AVS, either alone, or with one or more other criteria, such as for comparing different electrode configurations in the AVS. In an example, information about whether a particular electrode configuration can capture a desired resulting heart contraction, without resulting in phrenic nerve stimulation—which can trigger a hiccup-like contraction of the diaphragm, which is usually undesired—can be used as a criterion for AVS, either alone, or with one or more other criteria, such as for comparing the different electrode configurations in the AVS. The present inventors have recognized, among other things, that information about whether a particular electrode configuration results in one or more of anodal capture, cathodal capture, or both anodal capture and cathodal capture can be a useful input to AVS, for any of several reasons. In an example, such information can be used to intentionally select a configuration of two or more electrodes such as for intentionally providing a combination of both anodal and cathodal capture from at least two different local sites, such as described above, or for intentionally avoiding such concurrent anodal and cathodal capture, such as described above. In an example, information about whether a particular electrode configuration results in one or more of anodal capture, cathodal capture, or both anodal capture and cathodal capture can be a useful input to AVS, such as to select an electrode configuration that avoids phrenic nerve stimulation, or that promotes the desired form of capture while avoiding phrenic nerve stimulation. For example, in the context of AVS, it may be desirable to ensure that the anode is not the electrode that is causing the phrenic nerve stimulation.

Figure 4A:
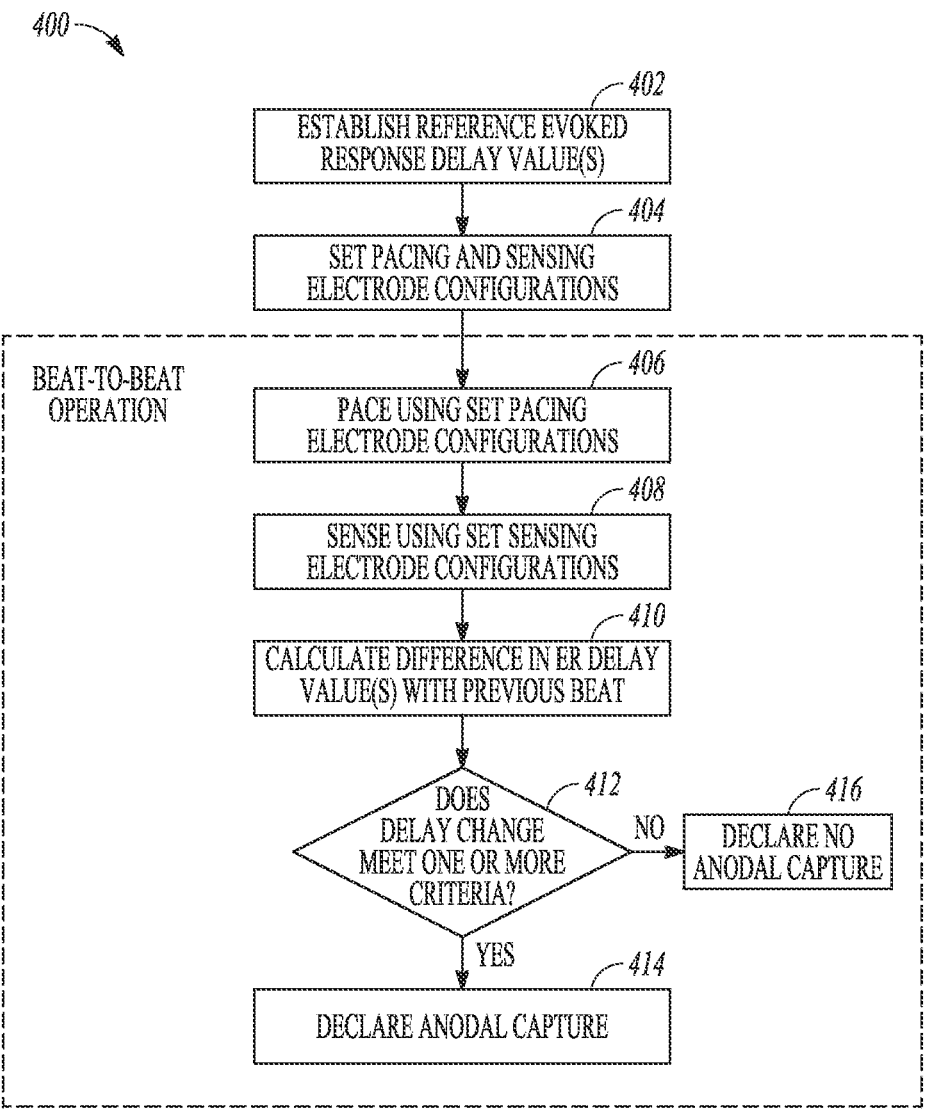
FIG. 4A shows an example of detecting at least partial anodal capture.

FIG. 4A shows an example 400 of detecting at least partial anodal capture. A cardiac signal sensing circuit (e.g., an atrial sensing circuit 108 or a ventricular sensing circuit 110) can detect an evoked response signal in response to electrostimulation. At 402, a first evoked response delay value can be established. In an example, this can include detecting (e.g., for a presumed anodal stimulation status) a time between an issued pace pulse and the resulting evoked response signal, or a feature thereof (e.g., first negative peak, most-negative peak, slope of the S-wave, or S wave width). The detected time interval for a single beat can be used, or a central tendency of such detected time intervals for multiple beats can be used. A presumed anodal stimulation status can be used, such as by using vastly different surface areas of the electrodes to ensure that capture occurs at the smaller surface-area electrode. For example, this can include using a unipolar pacing configuration between a small surface area lead electrode and a large surface area "can" electrode. If the small surface area lead electrode is used as the negative electrode, then cathodal stimulation can be presumed. If the small surface area lead electrode is used as the positive electrode, then anodal stimulation can be presumed. In an example, establishing the first evoked response delay can include receiving the reference evoked response delay value from a user input, or from a manufacturer-specified or other pre-specified value.

At 404, a pacing electrode configuration, for which anodal capture information is desired, can be specified. A corresponding evoked response sensing electrode configuration, for obtaining information for determining the anodal capture information, can be specified. This can include choosing a sensing electrode that is located near the pacing electrode for which anodal capture is to be determined.

At 406, paces can be issued, such as on a beat-to-beat basis using the specified pacing electrode configuration.

At 408, a corresponding ER can be sensed, such as on a beat-to-beat basis using the specified sensing electrode configuration. The corresponding ER can be used to determine an ER delay, such as between the issued pace pulse and a like ER feature to that which was used to determine the reference ER delay at 402. The ER delay can be determined from a single beat, or a composite ER delay can be computed such as by using a central tendency of ER delay values, such as computed for several respective beats.

At 410, the ER delay or composite ER delay determined at 408 can be compared to the reference ER delay determined at 402, or to a delay previously computed at 408 for a beat or group of beats.

At 412, a resulting difference can be compared to one or more criteria. If the difference exceeds one or more criteria, then, at 414, anodal capture can be declared, otherwise, at 416, it can be declared that no anodal capture is present.

Figure 4B:
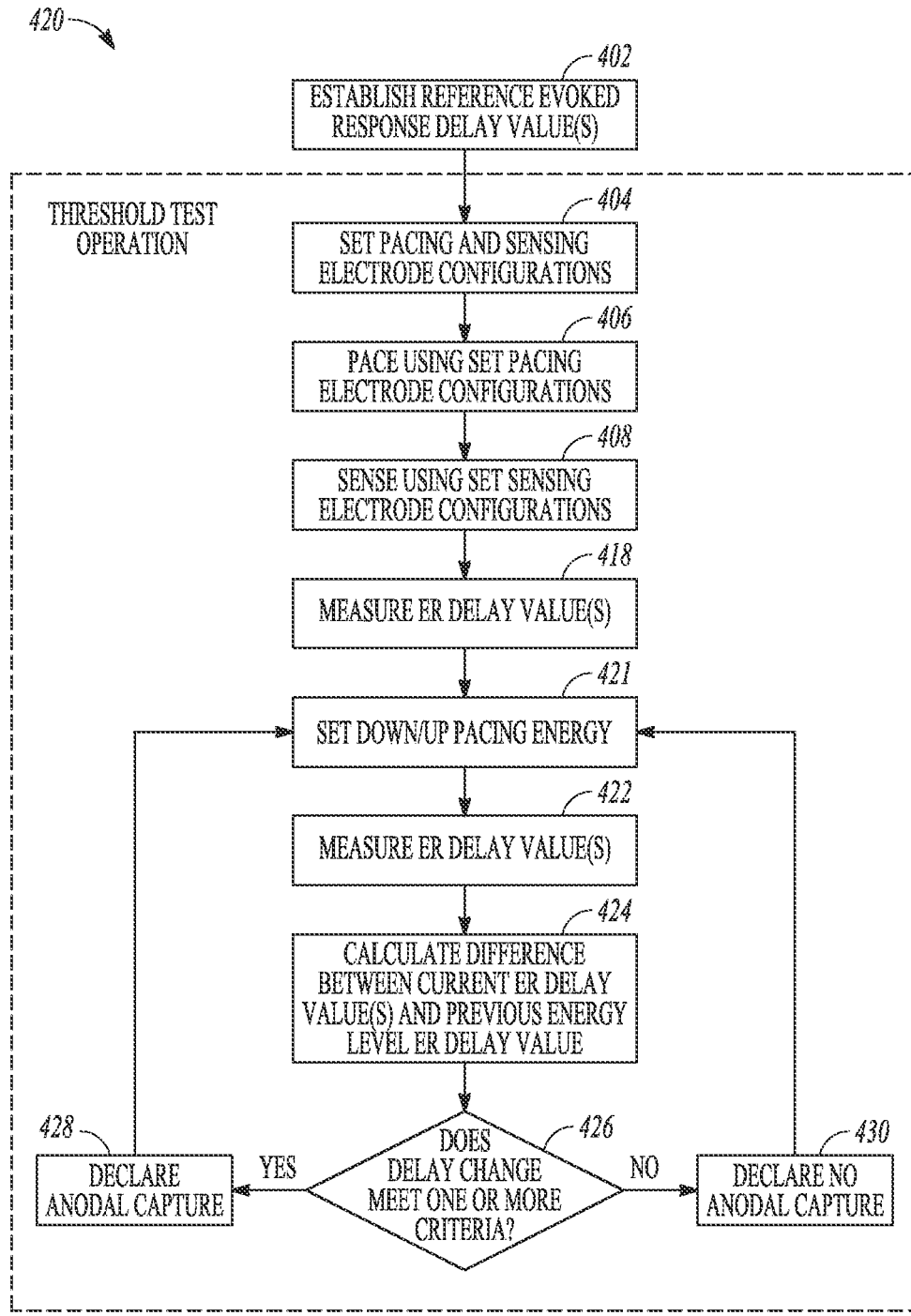
FIG. 4B shows an example of detecting at least partial anodal capture.

FIG. 4B shows an example 420 of detecting at least partial anodal capture, similar to that described above with respect to FIG. 4A, but focused on the context of a pacing energy threshold test, instead of being focused on the beat-to-beat operation described with respect to FIG. 4A. In FIG. 4B, at 402, a reference ER delay value can be established, such as described above with respect to FIG. 4A. At 404 of FIG. 4B, pacing and sensing electrode configurations can be established, such as described above with respect to FIG. 4A. At 406 of FIG. 4B, one or more pace pulses can be issued, such as described above with respect to FIG. 4A. At 408, corresponding ER signals can be sensed using the specified sensing electrode configuration, such as described above with respect to FIG. 4A. At 418, an ER delay value can be measured, such as described above with respect to 410 of FIG. 4A. At 421, a pacing energy (e.g., amplitude, pulsewidth, etc.) can be adjusted, such as by incrementally stepping it down (or up) such to an adjacent value in a set of available pacing energy values. At 422, the new pacing energy can be used to issue another pace, sense a resulting ER, and measure a resulting ER delay value, such as between the issued pace and a like ER feature to that which was used above in 418 and 402. At 424, the ER delay value can be compared to a corresponding value at the previous value of pacing energy. At 426, if the magnitude of the difference between the present and previous ER delay values meets one or more criteria, such as by exceeding a threshold amount, then, at 428, anodal capture can be declared, and process flow can return to 421, to repeat until one or more specified detection criteria (e.g., specified "X of Y" beats declared anodal captures) are met. At 426, if the magnitude of the difference between the present and previous ER delay values does not meet the one or more criteria, then, at 430, it is declared that the beat does not represent anodal capture, and process flow can return to 421, to repeat until one or more specified detection criteria (e.g., specified "X of Y" beats declared anodal captures) are met.

Figure 4C:
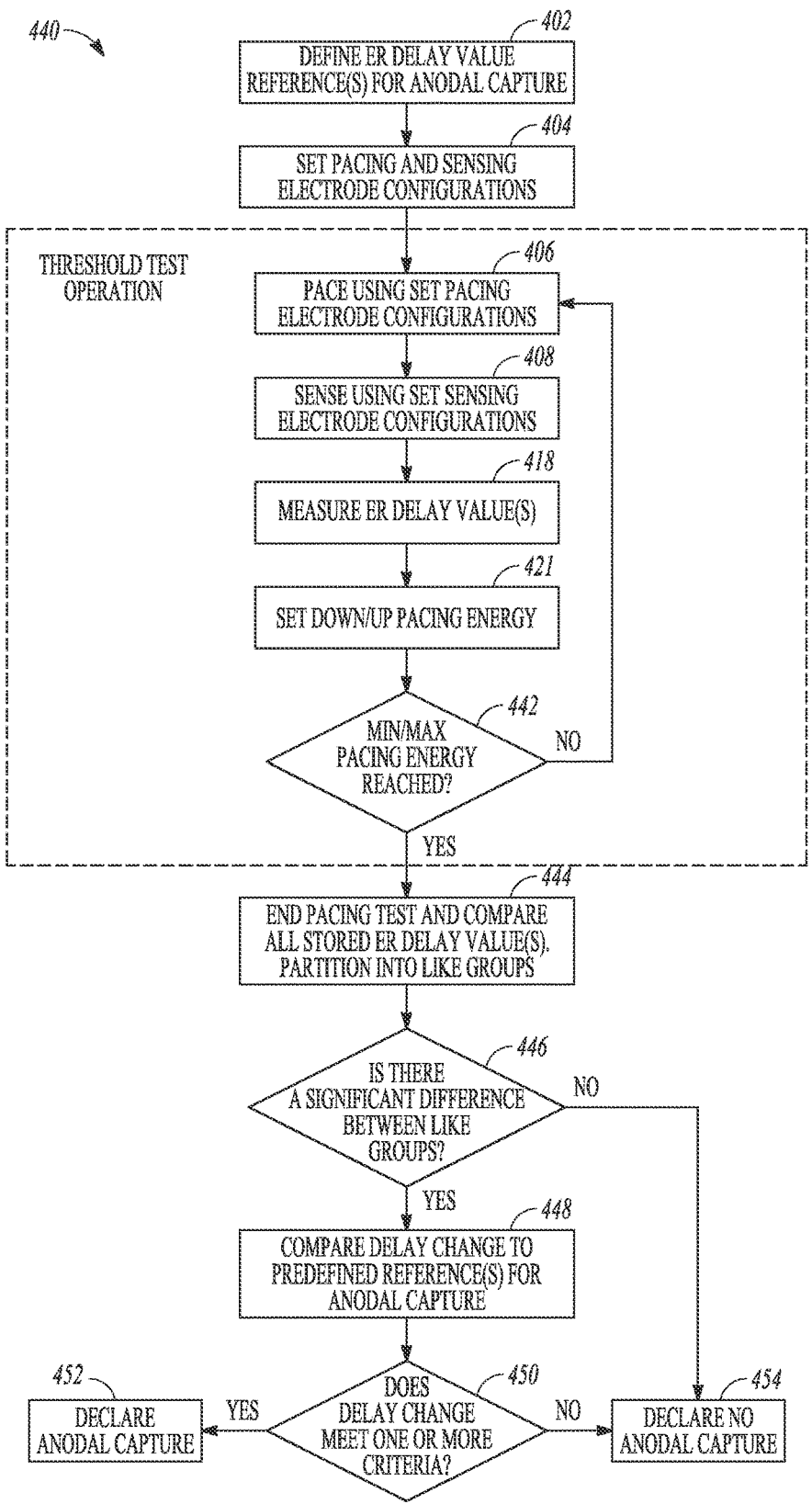
FIG. 4C shows an example of detecting at least partial anodal capture.

FIG. 4C shows an example 440 of detecting at least partial anodal capture, similar to that described above with respect to FIG. 4A, but focused on the context of a pacing energy threshold test, instead of being focused on the beat-to-beat operation of FIG. 4A. At 402, an ER delay reference value can be determined, such as described above with respect to FIG. 4A. At 404, pacing and sensing electrode configurations can be specified, such as described above with respect to FIG. 4A. A pacing energy threshold test can commence, such as by issuing a pace at 406, such as described above with respect to FIG. 4A. At 408, a resulting ER can be sensed, such as described above with respect to FIG. 4A. At 418, an ER delay value can be measured, such as described above with respect to FIG. 4A, and stored. At 421, the pacing energy can be adjusted, such as stepped down (or stepped up), such as described above with respect to FIG. 4B. If the threshold test pacing energy limit (e.g., lower limit, where the pacing energy is being stepped down, or the upper limit, where the pacing energy is being stepped up) is not reached, process flow can return to 406, otherwise, process flow can proceed to 444. At 444, the pacing energy threshold test is ended. The stored ER delay values corresponding to the various pacing energies used during the pacing energy threshold test can be partitioned into like groups (e.g., groups exhibiting a similar ER delay value). At 446, it can be determined whether there is a significant difference between the like groups. If so, then at 448, the ER delay values can be compared to the ER delay reference value determined at 402. If the difference meets one or more criteria (e.g., if the reference value is representative of anodal capture, and the difference falls below a specified value with respect to the reference value), then anodal capture can be declared at 452. Otherwise, at 454, it can be declared that no anodal capture has occurred.

Example A

Figure 4D:
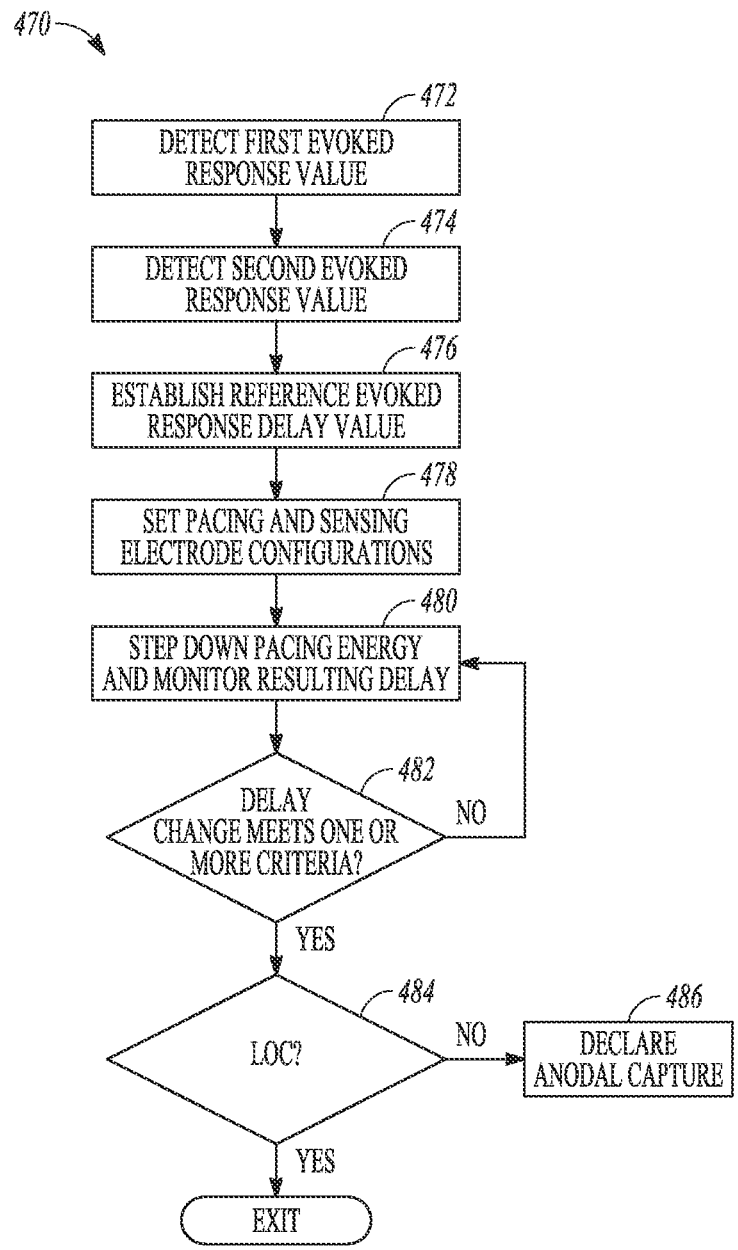
FIG. 4D shows an example of detecting at least partial anodal capture.

FIG. 4D shows an example 470 of detecting at least partial anodal capture. At 472, a first evoked response (ER) delay value can be detected. In an example, this can include detecting a time between an issued pace pulse and a resulting evoked response signal, or a specified feature thereof (e.g., first negative peak, most-negative peak, slope of the S-wave, or S wave width). In an example, this first ER delay can be measured in response to a pace delivered using a pacing electrode configuration that is unlikely to result in anodal capture, such as a unipolar pace between a cathodal LV electrode (e.g., one of LV ring electrode 214, LV tip electrode 212, LV ring electrode 302A-C, or LV tip electrode 302D) and a larger surface area "can" electrode 216 such as located at a housing of the electronics unit of the implantable device 102. Because the can electrode 216 has a substantially larger surface area than the cathodal LV electrode, and is generally pectorally-located at a substantial distance away from the heart, capture does not occur at the can electrode 216. Instead, capture only occurs at the cathodal LV electrode. By applying a negative voltage to the LV electrode, rendering it cathodal, any resulting capture will be cathodal. In this way, the first ER delay value can be representative of an ER delay that is associated with cathodal LV capture.

For sensing the ER delay, a sensing electrode configuration can be used that includes at least one electrode that is located close to a "candidate" electrode for which the presence or absence of stimulation is to be determined, or distant from another electrode with which the candidate electrode is to be used. In an example in which it is desired to be determine whether anodal capture is occurring at the RV ring electrode 208 when the RV ring electrode 208 is used as the anode together with an LV electrode (e.g., 212, 214, or one or more of 302A-D) as the cathode to deliver a pace, the ER sensing can be between the RV tip electrode 206 and a can electrode 216 or a header electrode 218. In this example, the RV tip electrode 206 is close to the candidate RV ring electrode 208 (to be tested for anodal capture) and distant from the LV electrode (e.g., 212, 214, or one or more of 302A-D) that is to be used together with the candidate RV electrode 208 to deliver the pace.

In an example in which the ER delay is measured between an issued pace and a resulting specified feature of the ER, some illustrative examples of such a feature can include a start of activation (e.g., such as can be determined by a level-detector circuit), a positive or negative peak of activation (e.g., such as can be determined by a peak detector circuit), or some other feature.

At 474, a second ER delay value can be detected. In an example, this can include detecting a time between an issued pace pulse and a resulting evoked response signal, or a specified feature thereof—such as a like feature to that described above with respect to 472.

In an example, this second ER delay can be measured using the candidate electrode to deliver a unipolar pace together with a can electrode 216. Again, because of the different electrode surface areas and the substantial distance between the can electrode 216 and the heart, capture will occur at the candidate electrode. Such capture will be cathodal when the candidate electrode is negative with respect to the can electrode 216 during the pace, and will be anodal when the candidate electrode is positive with respect to the can electrode during the pace. Either can be used, but cathodal stimulation at the can electrode 216 may be uncomfortable, and it should be noted that it is believed that anodal stimulation may propagate through tissue faster than cathodal stimulation. In any case, the resulting second ER delay will be representative of capture occurring at the candidate electrode. By contrast, the first ER delay described with respect to 472 will be representative of LV capture occurring away from the candidate electrode and the second ER delay will be representative of capture occurring at the candidate electrode. Since the unipolar sensing electrode (e.g., RV tip electrode 206) is closer to the candidate electrode than it is to the LV electrode to be used together with the candidate electrode, the second ER delay will be shorter than the first ER delay. Conversely, a different electrode configuration can be used in which the unipolar sensing electrode is farther from the candidate electrode and closer to the other electrode, in which case the first ER delay will be shorter than the second ER delay.

At 476, a reference ER delay value can be established, such as for later use to determine whether capture is occurring at or away from the candidate electrode. In an example, the reference ER delay can be established to be a specified (e.g., fixed percentage, etc.) increment shorter than the first ER delay value. In an example, the measured reference ER delay need not be generated using a single measurement, but can instead be generated using multiple measurements, such as a mean, median, or other central tendency of multiple measurements. In an example, the reference ER delay can be established to be a specified (e.g., fixed, percentage, etc.) increment longer than the second ER delay value. In an example, the reference ER delay can be established to be a desired fraction (e.g., midway) of the temporal distance between the first and second ER delay values.

At 478, the pacing and sensing electrode configurations can be established, such as for use in providing a step-down (or step-up) pacing energy threshold test, or on a beat-to-beat basis without requiring a pacing energy threshold test. In an example in which the candidate electrode being tested for anodal capture is the RV ring electrode 208, used in an extended bipolar pacing configuration with the other electrode being the LV ring electrode 214 (by way of example), a unipolar sensing configuration between the RV tip electrode 206 and the can electrode 216 can be used, such as described above.

At 480, in an example, the pacing energy can be set to an initial value, such as at or near the top of the pacing energy range. Then, the pacing energy can be stepped down and the resulting ER delay can be monitored. Conversely, the pacing energy can be set to an initial value, such as at or near the bottom of the pacing range, then the pacing energy can be stepped up and the resulting ER delay can be monitored. This can be done as part of a pacing energy threshold test, or on a beat-to-beat basis without requiring a pacing energy threshold test.

At 482, the resulting ER delay can be compared to one or more criteria, such as to the reference ER delay that was established at 406. If the resulting ER delay meets the criteria, such as by exhibiting a shift from longer than the reference ER delay to shorter than the reference ER delay, or vice-versa, then a change in capture is suspected. Otherwise, if the resulting ER delay does not meet the criteria, then the pacing energy can again be stepped down at 410 and the resulting delay can be monitored.

At 484, it can be determined whether complete LOC has occurred, such as by using existing automatic capture verification technique, such as described in—Meyer et al. U.S. Pat. No. 7,711,424, entitled SELECTION OF CARDIAC SIGNAL FEATURES DETECTED IN MULTIPLE CLASSIFICATION INTERVALS FOR CARDIAC PACING RESPONSE CLASSIFICATION, which is incorporated by reference herein. If at 484 no complete LOC has occurred, then at 486 it can be declared that anodal capture is likely present at the RV ring electrode 208 at energies that are greater than or equal to the particular pacing energy being used. Otherwise, at 482, if complete LOC has occurred, then it can be declared that cathodal capture at the LV ring electrode 214 (unaccompanied by anodal capture at the RV ring electrode 208) is likely present at energies that are greater than the particular pacing energy being used when the onset of complete LOC occurred.

In this way, by using a sensing electrode that is closer to a first pacing electrode than to a second pacing electrode, a shift in a resulting ER time can be used to determine whether one (or both) of these first and second pacing electrodes (or which one) is actually capturing nearby cardiac tissue. Since the polarity of the signals applied at the first and second pacing electrodes can be specified, such information can be used with the capture information to determine whether anodal capture is occurring, cathodal capture is occurring, or both anodal and cathodal capture are occurring.

If the pacing energy is being stepped down, a likely scenario can be that the resulting ER delay shifts from shorter (because the RV ring electrode 208 is exhibiting anodal capture at such higher pacing energies) to longer (when the RV ring electrode ceases anodal capture, and cathodal-only capture occurs at the LV ring electrode 214). It is believed that the ER delay can become even longer when complete LOC occurs (e.g., the LV ring electrode 214 is no longer exhibiting cathodal capture).

As a variation to the example describe above, detecting the first and second ER values at 402 and 404 can be replaced or augmented by detecting corresponding first and second ER signal templates. Then, at 412, the monitored ER morphology can be compared to one or both of the templates, such as by performing a correlation function. If the monitored ER morphology exhibits a sufficient shift away from the first ER signal template, or a sufficient shift toward the second ER signal template, or both, then a corresponding change in capture can be declared. Such replacing or augmenting an ER value (which can be compared to a reference value) with an ER signal template (to which a correlation function or other similarity calculation can be performed) can be extended to the ER values of various other examples described in this document.

Figure 5:
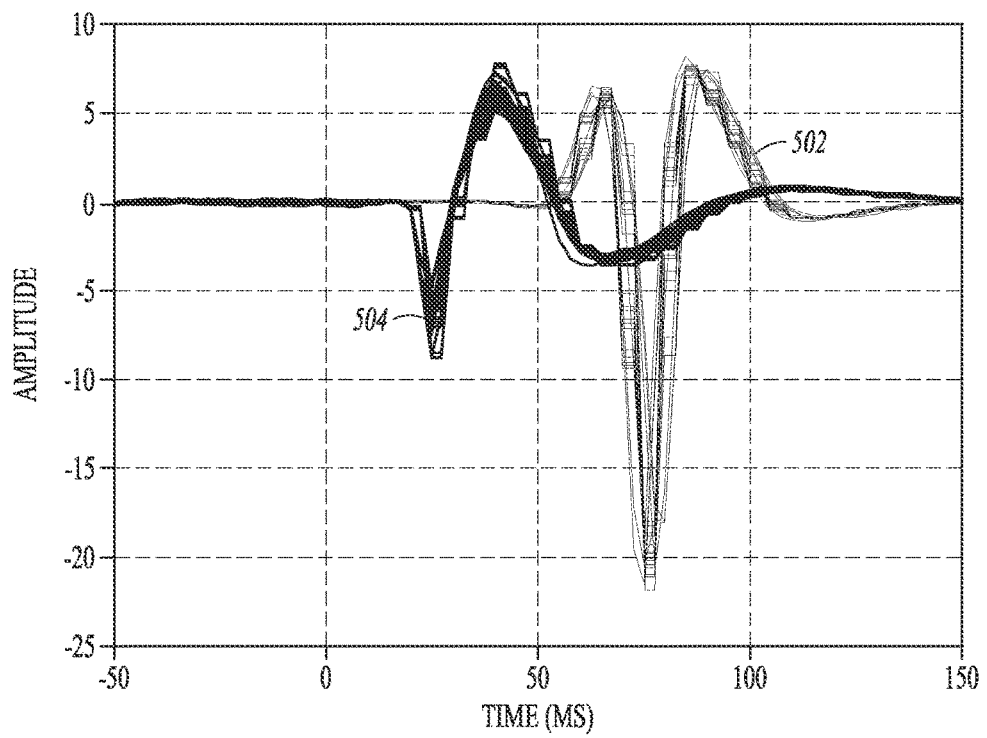
FIG. 5 is an amplitude vs. time graph of showing multiple tracings of ER signals resulting from cathodal-only capture and multiple tracings of ER signals resulting from combined anodal and cathodal capture.

FIG. 5 is an amplitude vs. time graph showing multiple tracings 502 of ER signals resulting from cathodal-only capture and multiple tracings 504 of ER signals resulting from combined anodal and cathodal capture. In the graph of FIG. 5, the pace pulse is issued at time t=0. For this example, extended bipolar pacing was delivered between the RV ring electrode 208 and one of the LV ring electrode 214 and the LV tip electrode 212, with the LV electrode being more negative than the RV electrode during the pace pulse. The ER signal was sensed using a unipolar sensing configuration between the RV tip electrode 206 and the can electrode 216.

In the example of FIG. 5, the combined anodal and cathodal capture ER signals 504 collectively exhibit an approximately 25 millisecond shorter delay from the preceding pace pulse than the cathodal-only capture ER signals 502, along with a noticeably different signal morphology. Such data supports the above-described examples, indicating that either the shift in time delay or change in ER signal morphology (or both) can be used to discriminate between cathodal-only capture and combined anodal and cathodal capture.

Example B

Figure 6:
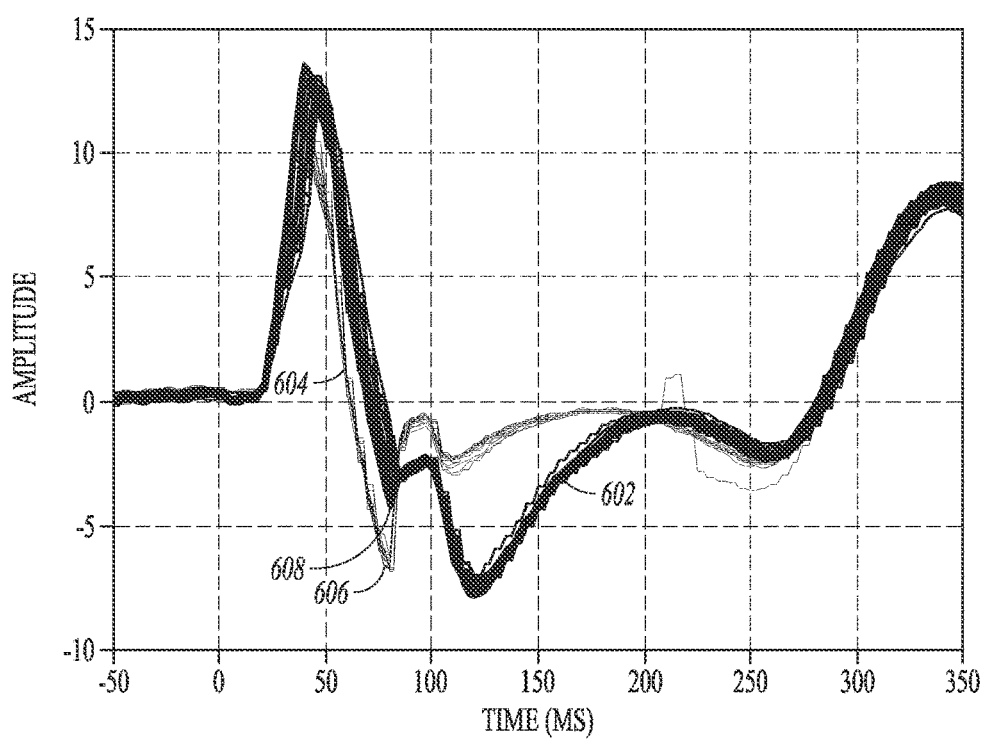
FIG. 6 is an amplitude vs. time graph showing multiple tracings of (1) cathodal-only capture ER signals and (2) combined anodal and cathodal ER signals.

FIG. 6 is an amplitude vs. time graph showing multiple tracings of (1) cathodal-only capture ER signals 602 and (2) combined anodal and cathodal ER signals 604. In an example, such as illustrated with respect to FIG. 6, the candidate electrode being tested to determine whether anodal capture is occurring can be the RV ring electrode 208, which can be used in an extended bipolar pacing configuration with one of the LV ring electrode 214 or the LV tip electrode 212, with unipolar ER signal sensing carried out between the can electrode 216 and the other one of the LV ring electrode 214 and the LV tip electrode 212.

In the example of FIG. 6, differences can be observed between the cathodal-only capture ER signals 602 and the combined anodal and cathodal ER signals 604. In particular the first negative peak 606 of the combined anodal and cathodal ER signals 604 occurs some time (e.g., 30 to 40 milliseconds, although this can vary) earlier than the corresponding first negative peak 608 of the cathodal-only capture ER signals 602. Such a time difference can be used to detect a shift from cathodal-only capture to combined anodal and cathodal capture, or vice-versa. Moreover, such a difference in the ER signal can be used in either a cross-chamber (e.g., extended bipolar) setting, such as shown in FIG. 2, or in a within-chamber (e.g., LV quadripolar such as shown in FIG. 3, RV bipolar, etc.) setting such as to perform such discrimination between cathodal-only capture and combined anodal and cathodal capture.

Figure 7:
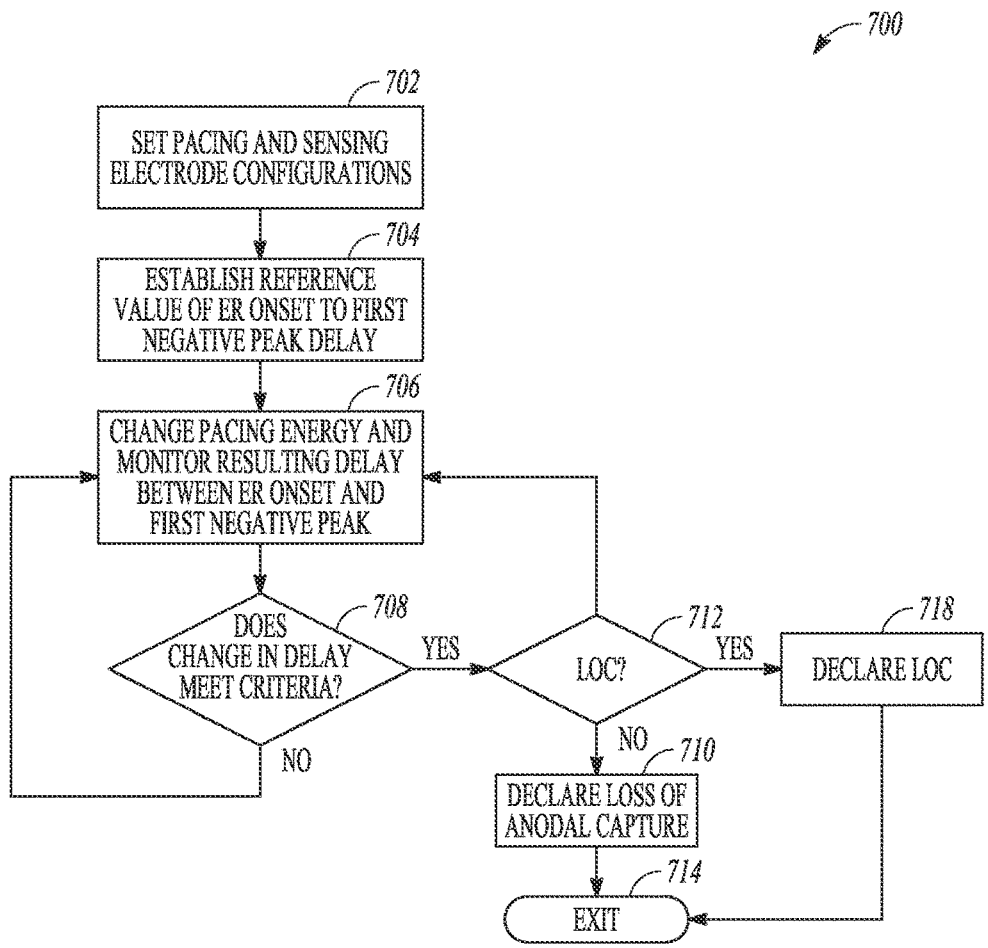
FIG. 7 shows an example of detecting anodal capture, such as by using the temporal shift of the first negative peak of the ER signal, such as shown in FIG. 6.

FIG. 7 shows an example 700 of detecting anodal capture, such as by using the temporal shift of the first negative peak of the ER signal, such as shown in FIG. 6. At 702, pacing and sensing electrode configurations can be set, such as appropriate for obtaining a reference value of the time interval between (1) a reference fiducial, such as the onset of the ER activation and (2) the first negative peak of the ER signal. In an example, the pacing and sensing electrode configurations can be set such that the reference value of the time interval can be obtained in a manner such that it is known whether anodal stimulation is occurring, such as described above. In an example, the candidate electrode being tested to determine whether anodal capture is occurring can be the RV ring electrode 208, which, in an example, can be used in an extended bipolar pacing configuration with at least one of the LV ring electrode 214 or the LV tip electrode 212 (or other left ventricular electrode, such as with a multipolar, e.g., quadripolar, LV lead), with unipolar ER signal sensing carried out between the can electrode 216 and the other one of the LV ring electrode 214 and the LV tip electrode 212. At 702, the pacing and sensing electrode configurations can be set accordingly.

At 704, the pacing and sensing electrode configurations of 702 can be used to obtain a reference value of the time interval between (1) the onset of the ER activation and (2) the first negative peak of the ER signal. This can include using the controller circuit 116 to direct the ventricular therapy circuit 114 to issue a pacing pulse, such as using the pacing electrode configuration described above, and using the controller circuit 116 to direct the ventricular sensing circuit 112 to sense the ER signal. The resulting ER signal can be analyzed, such as by using signal processing circuitry that can be provided by the controller circuit 116 or elsewhere, such as to detect the onset of the ER activation (e.g., using a level detector circuit that can be provided by such signal processing circuitry) and to detect the subsequent first negative peak of the ER signal (e.g., using a peak-detector circuit that can be provided by such signal processing circuitry), and measuring a time difference between the onset of the ER activation and the subsequent first negative peak of the ER signal. This measured time difference can be used as a reference time difference, such as to which later time difference measurements can be compared. As explained above, the reference time difference can be obtained under a known condition of whether anodal stimulation is present, which can provide useful contextual information as other measurements later deviate toward or away from the reference time difference value. In an example, the measured reference time difference need not be generated using a single measurement, but can instead be generated using multiple measurements, such as a mean, median, or other central tendency of multiple measurements. In an example, multiple measurements used to generate the reference time difference can be made using like pacing energies, such as at a large pacing energy value, for example, maximum pacing amplitude at a nominal pacing pulsewidth (e.g., 0.4 milliseconds or 0.5 milliseconds).

At 706, the pacing energy can be adjusted, for example, decreased, such as by stepping the pacing energy down incrementally. In an example, this can include decreasing the pacing amplitude incrementally while maintaining a specified pacing pulsewidth, or vice-versa. In an example, at each such step, an ER signal is obtained, and the time difference between the onset of the ER activation and the subsequent first negative peak can be obtained. As described above with respect to the reference time difference, for a particular pacing energy step this can be determined using a single measurement, or by computing a central tendency or otherwise combining the time differences resulting from multiple individual measurements, such as from corresponding multiple ER signals associated with corresponding multiple paces.

At 708, the resulting measured time difference (or resulting combined measured time difference) can be compared to one or more criteria. In an example, this can include comparing the resulting measured time difference to a threshold value that can be based upon the reference time difference, such as a percentage thereof, a fixed offset therefrom, or the like. In an illustrative example, it can be known or assumed that anodal capture is occurring when the maximum pacing energy is delivered, such as for obtaining the reference time difference value at 704. In such a case, if at 708 the measured time difference increases above a specified percentage (e.g., 120%) of the reference time difference, then loss of anodal capture can be declared, and at 712, it can be determined whether complete loss of capture (LOC) has occurred at that particular increment of pacing energy. If there is no complete LOC, then at 710, loss of anodal capture can be declared, and the example 700 can be exited at 714 (or can return to 706 if it is desired to also locate the energy at which complete LOC occurs). At 712, if there is complete LOC, then complete LOC can be declared at 718, and the example 700 can exit at 714. At 708, if the measured time difference does not meet the criteria (e.g., does not increase above 120% of the reference time difference value), then there can be a return to 706, and the pacing energy can be stepped down again, while monitoring the resulting ER signal to measure the resulting delay between the ER activation onset and the subsequent first negative peak, as described above.

Example C

Figure 8:
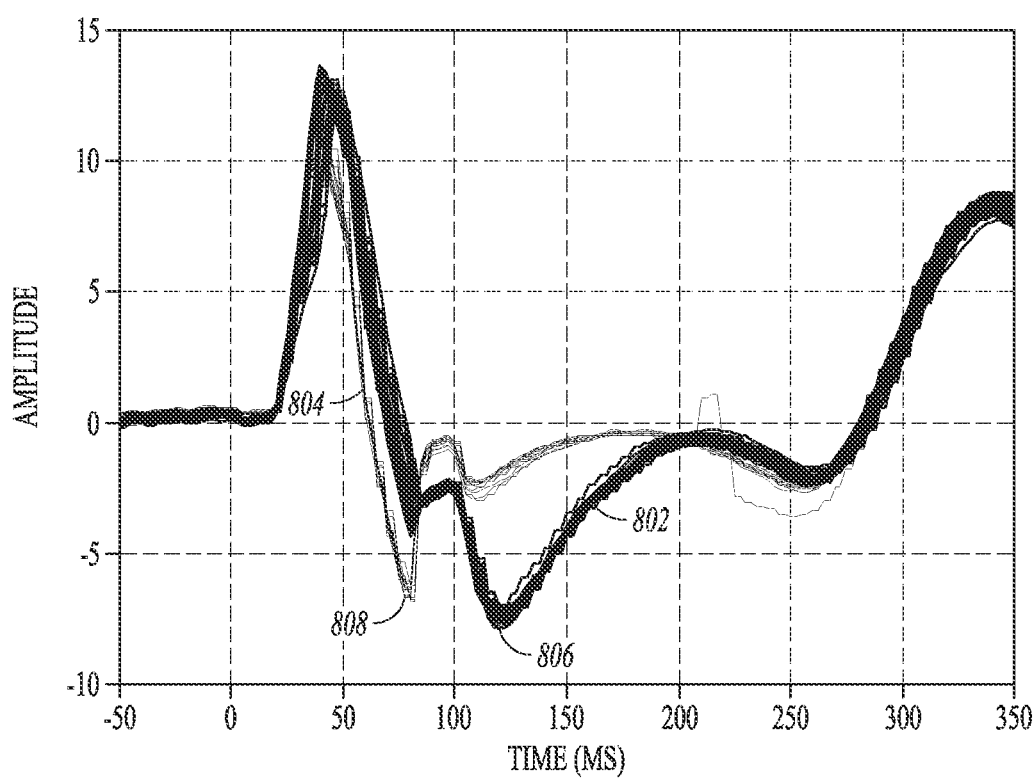
FIG. 8 is an amplitude vs. time graph showing multiple tracings of (1) cathodal-only capture ER signals and (2) combined anodal and cathodal ER signals, in which a different electrode configuration can be used for obtaining a reference time difference than for determining a later time difference.

In the example of FIG. 7, the same pacing electrode configuration and sensing electrode configuration can be used both for determining the reference time difference at 704 and for determining the later time differences at 706. However, this is not required. In an example, a different electrode configuration can be used for obtaining a reference time difference than for determining a later time difference. For example, FIG. 8 is an amplitude vs. time graph showing multiple tracings of (1) cathodal-only capture ER signals 802 and (2) combined anodal and cathodal ER signals 804. In this example, the various ER signal tracings are temporally aligned, such as according to a previous pace or according to the onset of the ER activation. In an example, such as illustrated with respect to FIG. 8, the cathodal-only ER signals 802 can be used to form an ER signal reference template, such as can be obtained by delivering a unipolar LV pace, such as between a cathodal LV ring electrode 214 and an anodal can electrode 216, and unipolar ER signal sensing carried out between the can electrode 216 and the LV tip electrode 212. Delivering the unipolar LV pace in this manner assures that no anodal capture occurs, because of the distance between the anodal can electrode 216 and the excitable heart tissue, and the relatively larger surface area of the can electrode relative to the cathodal LV ring electrode 214. In this example, a reference time difference can be measured between the ER activation onset and the absolute minimum (e.g., the most negative peak 806) of the ER waveform (which is not necessarily the same as the first negative peak of the ER waveform described above with respect to FIG. 6).

Then, during a pacing energy threshold or capture test, or on a beat-to-beat basis outside of a threshold or capture test, a candidate electrode configuration can be tested to determine whether anodal capture is occurring. In an example, the candidate electrode being tested to determine whether anodal capture is occurring can be the RV ring electrode 208, which can be used in an extended bipolar pacing configuration with the same pacing cathode as was used to obtain the reference signal (e.g., such as the same LV ring electrode 214 used as the cathode in obtaining the reference signal, above), with unipolar ER signal sensing carried out between the can electrode 216 and an electrode near the pacing cathode (e.g., sensing using the LV tip electrode 212 when the LV ring electrode 214 is used as the pacing cathode). For each incremental change in the pacing energy, a time difference can be measured between the onset of the ER activation and the absolute minimum (e.g., the most negative peak 808) of the ER waveform (which is not necessarily the same as the first negative peak of the ER waveform described above with respect to FIG. 6). When the capture is at least in part anodal, the time difference will be considerably shorter than the reference time difference, such as, for example, about 40 milliseconds shorter as shown in the example of FIG. 8, although this number can vary, such as between patients. Thus, by comparing the time difference obtained using the ER signal 804 after the incremental change to one or more criteria derived from the reference time difference obtained using the ER signal 802, when the time difference drops below the reference time difference by more than a relative threshold value (e.g., 80% of the reference time difference) or by more than a fixed threshold value (e.g., by at least 25 milliseconds), then at least partial anodal capture can be declared. This can be based upon a single measurement, or multiple measurements (e.g., a central tendency), for either the reference time difference, or for the actual time differences obtained during various pacing energies.

Figure 9:
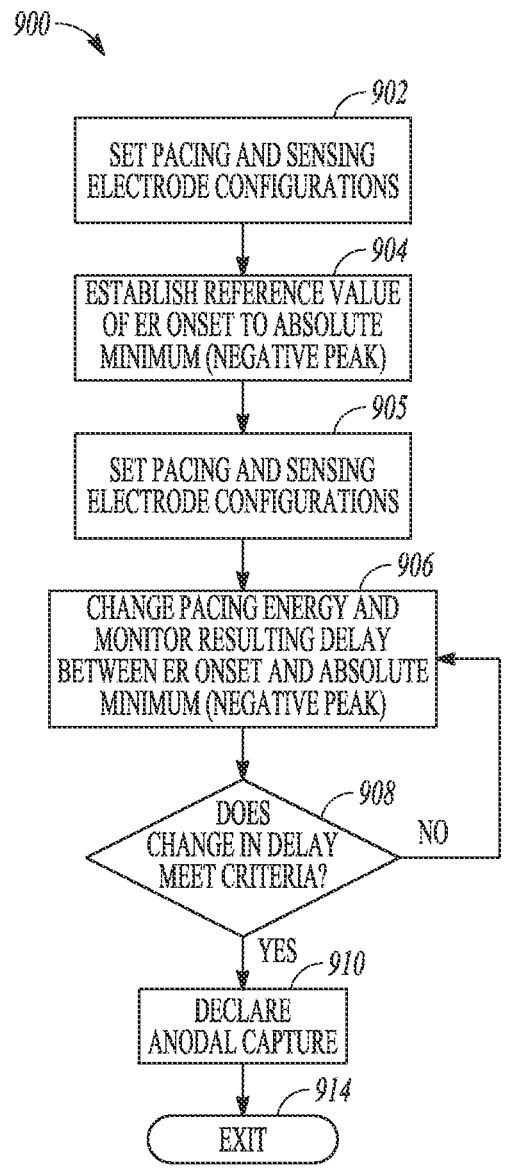
FIG. 9 shows an example 900 of detecting anodal capture, such as by using the temporal shift of the absolute minimum negative peak of the ER signal, such as shown in FIG. 8.

FIG. 9 shows an example 900 of detecting at least partial anodal capture, such as by using the temporal shift of the absolute minimum negative peak of the ER signal, such as shown in FIG. 8. At 902, pacing and sensing electrode configurations can be set, such as appropriate for obtaining a reference value of the time interval between (1) the onset of the ER activation and (2) the absolute minimum (most negative peak) of the ER signal, such as in a unipolar pacing and sensing configuration such as described above, for example, with respect to FIG. 8.

At 904, the pacing and sensing electrode configurations of 902 can be used to obtain a reference value of the time interval between (1) a reference fiducial, such as the onset of the ER activation and (2) the absolute minimum (most negative peak) of the ER signal, similar to that described above at 704, but using the absolute minimum (most negative peak) of the ER signal. This measured time difference can be used as a reference time difference, such as to which later time difference measurements can be compared, similar to that described above at 704, but using the absolute minimum (most negative peak) of the ER signal.

At 905, the pacing configuration can be changed, such as to apply the pacing configuration of interest for determining whether at least partial anodal capture is occurring. In an example, this can include placing the pacing electrode configuration into an extended bipolar pacing configuration, such as using the RV ring electrode 208 with the same one of the LV ring electrode 214 or the LV tip electrode 212 that was used as a pacing cathode for determining the reference value of the time interval at 904 with unipolar ER signal sensing carried out between the can electrode 216 and the other one of the LV ring electrode 214 and the LV tip electrode 212.

At 906, the pacing energy can be changed, similar to that described above with respect to 706, and a responsive ER signal fiducial can be acquired, such as described above, but using the absolute minimum (most negative peak) of the ER signal.

At 908, the resulting measured time difference (or resulting combined measured time difference) can be compared to one or more criteria, such as described above with respect to 708, although different criteria can be experimentally or otherwise determined and used here.

In an illustrative example, if at 908 the measured time difference falls below 80% of the reference time difference, then at 910, at least partial anodal capture can be declared, and at 914, the example 900 can be exited. Otherwise, there is a return to 906, and the pacing energy can be changed (e.g., stepped down) again, while monitoring the resulting ER signal to measure the resulting delay between the ER activation onset and the absolute minimum (most negative peak), as described above with respect to FIGS. 8-9.

Example D

Figure 10:
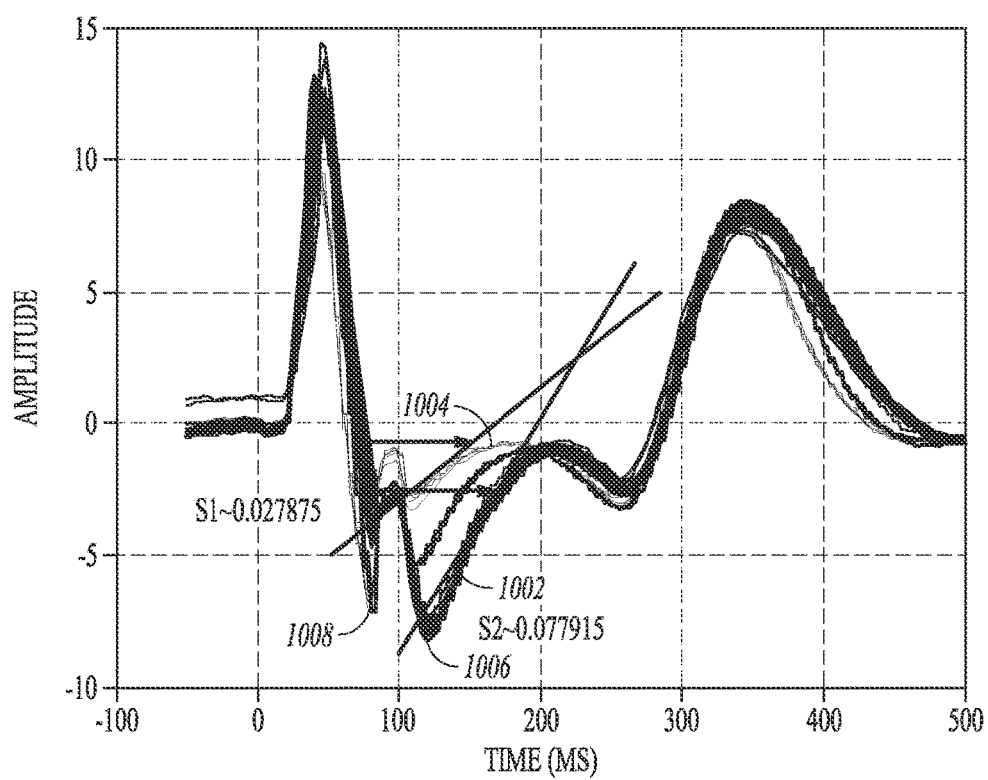
FIG. 10 is an amplitude vs. time graph showing multiple tracings of (1) cathodal-only capture ER signals and (2) combined anodal and cathodal ER signals.

FIG. 10 is an amplitude vs. time graph showing multiple tracings of (1) cathodal-only capture ER signals 1002 and (2) combined anodal and cathodal ER signals 1004. In this example, the various ER signal tracings are temporally aligned, such as according to a previous pace or according to the onset of the ER activation. In an example, such as illustrated with respect to FIG. 10, the cathodal-only ER signals 1002 can be used to form an ER signal reference template, for example, which can be obtained by delivering a unipolar LV pace, such as between a cathodal LV ring electrode 214 and an anodal can electrode 216, and unipolar ER signal sensing carried out between the can electrode 216 and the LV tip electrode 212. Delivering the unipolar LV pace in this manner assures that no anodal capture occurs, because of the distance between the anodal can electrode 216 and the excitable heart tissue, and the relatively larger surface area of the can electrode relative to the cathodal LV ring electrode 214. In this example, a reference S-wave slope of the ER signal can be measured after the absolute minimum (e.g., the most negative peak 1006) of the ER waveform (which is not necessarily the same as the first negative peak of the ER waveform described above with respect to FIG. 6) and before the next positive peak of the ER waveform.

Then, after an incremental pacing energy change, a candidate electrode configuration can be tested to determine whether at least partially anodal capture is occurring. In an example, the candidate electrode being tested to determine whether at least partially anodal capture is occurring can be the RV ring electrode 208, which can be used in an extended bipolar pacing configuration with one of the LV ring electrode 214 or the LV tip electrode 212, such as with unipolar ER signal sensing that can be carried out between the can electrode 216 and the other one of the LV ring electrode 214 and the LV tip electrode 212. For each incremental change in the pacing energy, an S-wave slope can be measured during all or a portion of a time between the absolute minimum (e.g., the most negative peak 1008) of the ER waveform (which is not necessarily the same as the first negative peak of the ER waveform described above with respect to FIG. 6) and the next positive peak of the ER waveform. When the capture is at least in part anodal, the S-wave slope will be considerably flatter (e.g., 0.027875, in an illustrative example for a particular patient) than the reference S-wave slope (e.g., 0.077915, in this illustrative example), such as shown by way of example, but not by way of limitation, in the illustrative example of FIG. 10. Thus, by comparing the S-wave slope obtained using the ER signal 1004 during the incremental change (e.g., step-up in pacing energy) to one or more criteria derived from the reference S-wave slope obtained using the ER signal 1002, when the S-wave slope drops below the reference S-wave slope by more than a relative threshold value (e.g., 80% of the reference S-wave slope, as an illustrative example) or by more than a fixed threshold value (e.g., by at least 0.025, as an illustrative example), then at least partially anodal capture can be declared. This can be based upon a single measurement, or multiple measurements (e.g., a central tendency), for either the reference S-wave slope, or for the actual S-wave slopes obtained during the incremental change (e.g., step-up, step-down, etc.) of pacing energies.

Figure 11:
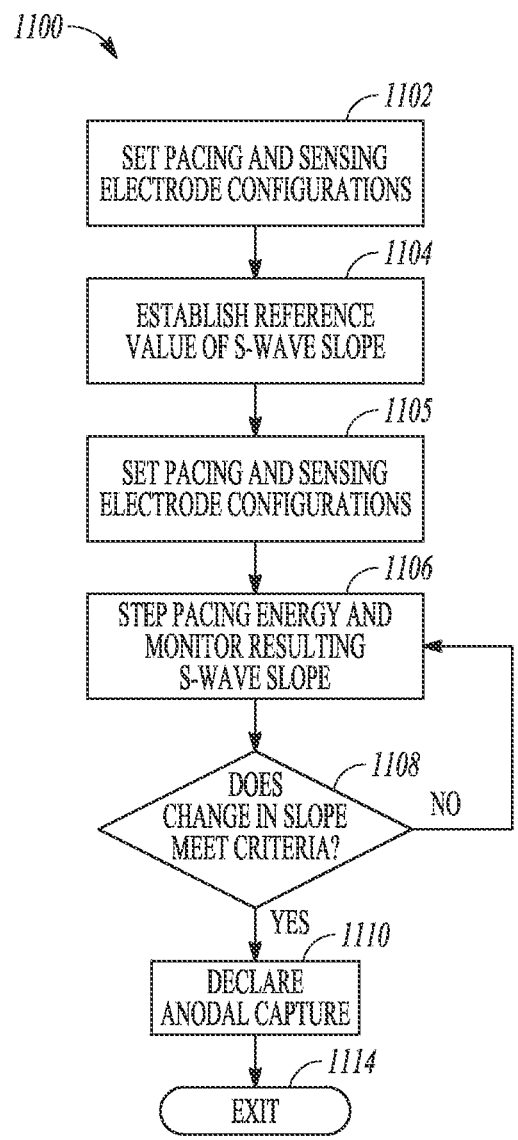
FIG. 11 shows an example of detecting anodal capture, such as by using the change of the S-wave slope of the ER signal, such as shown in FIG. 10.

FIG. 11 shows an example 1100 of detecting anodal capture, such as by using the change of the S-wave slope of the ER signal, such as shown in FIG. 10. At 1102, pacing and sensing electrode configurations can be set, such as appropriate for obtaining a reference value of the S-wave slope, such as described above with respect to FIG. 10.

At 1104, the pacing and sensing electrode configurations of 1102 can be used to obtain a reference value of the S-wave slope, similar to that described above at with respect to FIG. 10. This measured S-wave slope can be used as a reference S-wave slope, such as to which later S-wave slope measurements can be compared, similar to that described above with respect to FIG. 10. A central tendency of multiple measured S-wave slopes can be used to determine the reference S-wave slope, such as described above with respect to FIG. 10.

At 1105, the pacing configuration can be changed, such as to apply the pacing configuration of interest for determining whether at least partially anodal capture is occurring. In an example, this can include placing the pacing electrode configuration into an extended bipolar pacing configuration, such as described above with respect to FIG. 10.

At 1106, the pacing energy can be changed, such as by stepping the pacing energy up incrementally.

At 1108, the resulting measured S-wave slope (or resulting combined measured S-wave slope) can be compared to one or more criteria, similar to that described above with respect to 908, although different criteria can be experimentally or otherwise determined and used here.

In an illustrative example, if at 1108 the measured S-wave slope falls below 80% of the reference S-wave slope, then at 1110, anodal capture can be declared, and at 1114, the example 1100 can be exited. Otherwise, there is a return to 1106, and the pacing energy can be stepped up again, while monitoring the resulting ER signal to measure the resulting S-wave slope, as described above with respect to FIG. 10.

Figure 12:
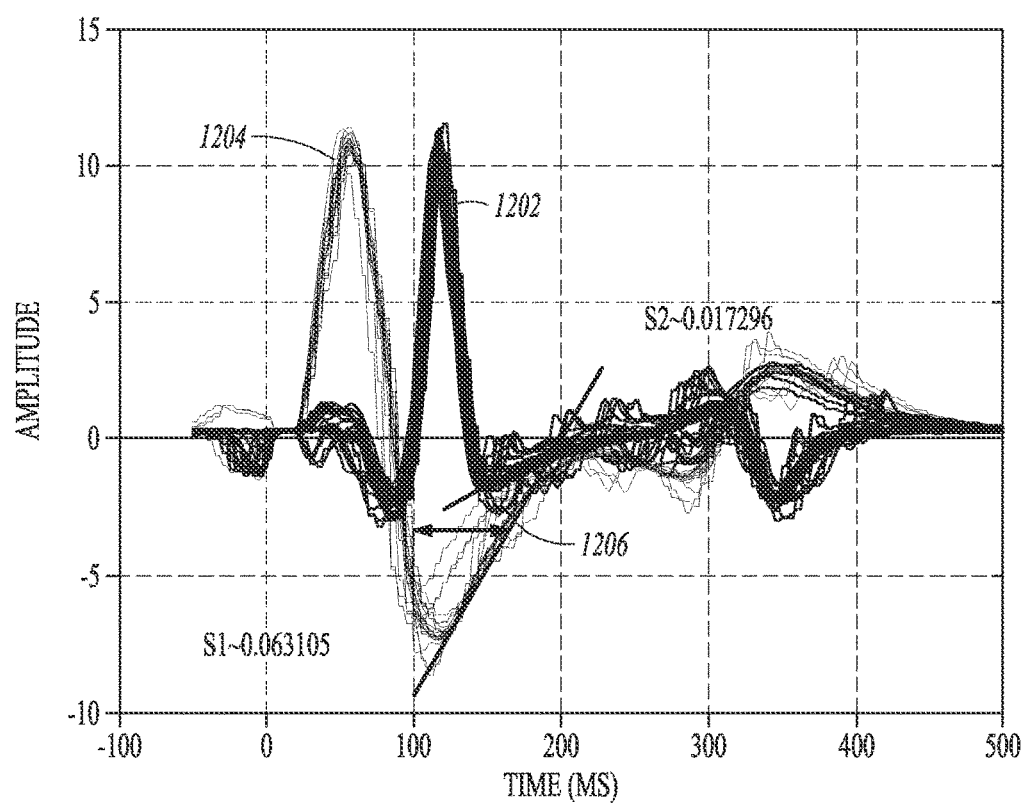
FIG. 12 is an amplitude vs. time graph showing multiple tracings of (1) cathodal-only capture ER signals and (2) combined anodal and cathodal ER signals, such as can be obtained using a "wide bipolar" pacing configuration.

FIG. 12 is an amplitude vs. time graph showing multiple tracings of (1) cathodal-only capture ER signals 1202 and (2) combined anodal and cathodal ER signals 1204. In this example, the various ER signal tracings are temporally aligned, such as according to a previous pace or according to the onset of the ER activation. In an example, such as illustrated with respect to FIG. 12, the cathodal-only ER signals 1202 can be used to form an ER signal reference template. In an example, the candidate electrode being tested to determine whether at least partially anodal capture is occurring can be the LV ring electrode 302A, which can be used in a "wide bipolar" pacing configuration, such as in which pacing pulses can be delivered between the proximal LV ring electrode 302A and the distal LV tip electrode 302D, such as with unipolar ER signal sensing that can be carried out between the can electrode 216 and another LV electrode such as a different one of the LV ring electrodes 302B or 302C and the distal LV tip electrode 302D.

In this example, a reference S-wave slope of the ER signal can be measured during all or a portion of a time period that is after the completion of the R-wave at 1206 of the ER waveform and before the next positive peak of the ER waveform. In an example, this can include using an electrode configuration that can be expected to yield cathodal only capture, such as described above.

Then, after a pacing energy step-up, a candidate electrode configuration can be tested to determine whether at least partially anodal capture is occurring. In an example, the candidate electrode being tested to determine whether at least partially anodal capture is occurring can be the proximal LV ring electrode 302A, which can be used in the above-described wide bipolar pacing configuration such as in which pacing pulses can be delivered between the proximal LV ring electrode 302A and the distal LV tip electrode 302D, with unipolar ER signal sensing carried out between the can electrode 216 and any other LV electrode such as a different one of the LV ring electrodes 302B or 302C and the distal LV tip electrode 302D.

For each incremental step-up in the pacing energy, an S-wave slope can be measured after the completion of the R-wave at 1206 of the ER waveform and before the next positive peak of the ER waveform.

When the capture is at least in part anodal, the S-wave slope will be considerably steeper (e.g., 0.017296, in an illustrative example) than the reference S-wave slope (e.g., 0.063105, in an illustrative example), such as shown by way of example, but not by way of limitation in the illustrative example of FIG. 12. Thus, by comparing the S-wave slope obtained using the ER signal 1204 during the incremental step-up to one or more criteria derived from the reference S-wave slope obtained using the ER signal 1202, when the S-wave slope increases above the reference S-wave slope by more than a specified relative threshold value (e.g., 120% of the reference S-wave slope, as an illustrative example) or by more than a specified fixed threshold value (e.g., by at least 0.023, in an illustrative example), then at least partially anodal capture can be declared. This can be based upon a single measurement, or multiple measurements (e.g., a central tendency), for either the reference S-wave slope, or for the actual S-wave slopes obtained during the step-down of pacing energies. The method can be carried out as described with respect to FIG. 11, except that the S-wave slopes can be obtained and the comparison to one or more criteria can be performed such as described with respect to the data shown in FIG. 12.

Example E

Figure 13:
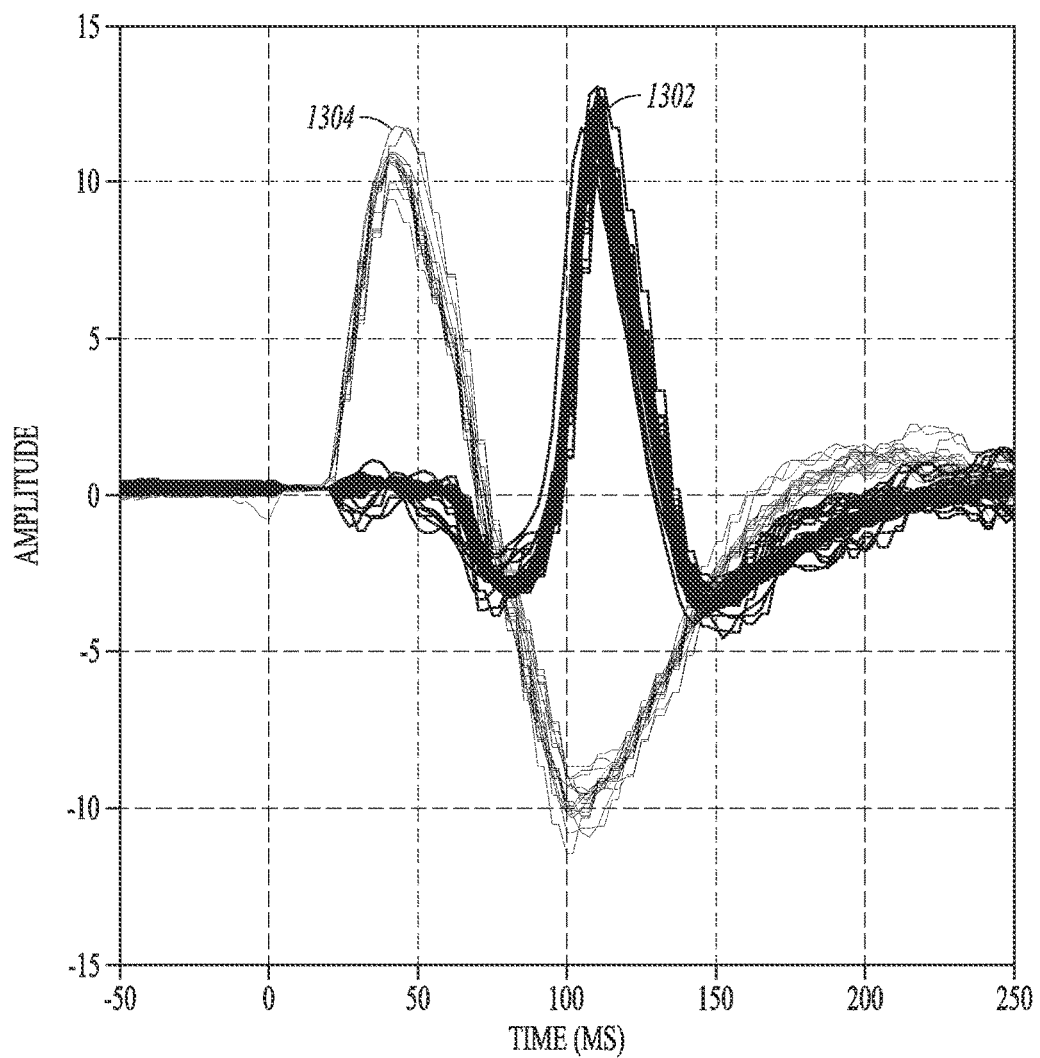
FIG. 13 is an amplitude vs. time graph showing multiple tracings of (1) cathodal-only capture ER signals and (2) combined anodal and cathodal ER signals, such as can be obtained using a "wide bipolar" pacing configuration.

FIG. 13 is an amplitude vs. time graph showing multiple tracings of (1) cathodal-only capture ER signals 1302 and (2) combined anodal and cathodal ER signals 1304, such as in which the sensing electrode that is used to record the ER can be closer to the anode than the cathode In this example, the various ER signal tracings can be temporally aligned, such as according to the issuance of an electrostimulation (e.g., pace) pulse. In an example, such as illustrated with respect to FIG. 13, the cathodal-only ER signals 1302 can be used to form an ER signal reference template. In an illustrative example, the candidate electrode being tested to determine whether at least partially anodal capture is occurring can be the LV ring electrode 302C, which can be used in a "wide bipolar" pacing configuration, such as in which pacing pulses can be delivered between the proximal LV ring electrode 302C (as an anode) and the distal LV tip electrode 302D (as a cathode), with ER signal sensing carried out between the the LV ring electrode 302B and the can electrode 216. Other wide bipolar pacing configurations are possible, such as using other multipolar leads.

In the example of FIG. 13, a time delay can be measured from the issuance of the pace pulse to the onset of the ER activation, such as which can be detected using a level detector circuit or the like. Because the ER signal sensing can be carried out using an electrode (e.g., LV ring electrode 302B) that is near the anode (e.g., LV ring electrode 302C), the pace-to-activation time delay observed will decrease upon transition from cathodal-only capture to at least partially anodal capture, such as an approximately 50 millisecond decrease shown by way of example, but not by way of limitation, in the illustrative example FIG. 13, which was not obtained from a human subject, but rather from a canine without heart failure.

Figure 14:
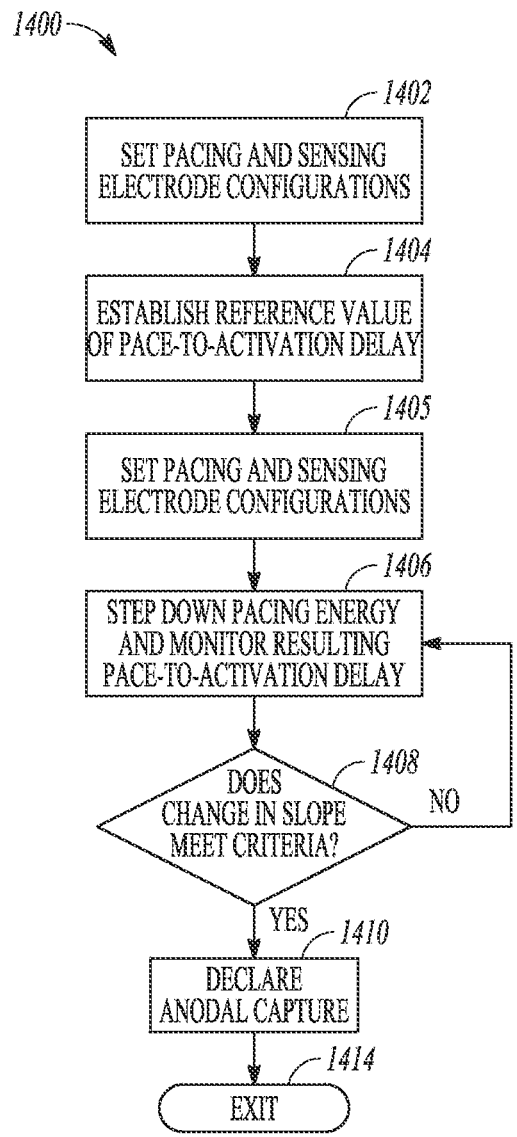
FIG. 14 shows an example of detecting anodal capture, such as by using the change of the pace-to-activation delay of the ER signal, such as shown in FIG. 13.

FIG. 14 shows an example 1400 of detecting anodal capture, such as by using the change of the pace-to-activation delay of the ER signal, such as shown in FIG. 13. At 1402, pacing and sensing electrode configurations can be set, such as appropriate for obtaining a reference value of the pace-to-activation delay of the ER signal, such as described above with respect to FIG. 13.

At 1404, the pacing and sensing electrode configurations of 1402 can be used to obtain a reference value of the pace-to-activation delay of the ER signal, similar to that described above at with respect to FIG. 13. This measured pace-to-activation delay of the ER signal can be used as a reference pace-to-activation delay of the ER signal, such as to which later pace-to-activation delay measurements can be compared, similar to that described above with respect to FIG. 13. In an example, the reference value can be obtained using a configuration that is unlikely to result in anodal capture (e.g., using the can electrode 216 as the anode). In an example, the reference value obtained can be presumed to be cathodal-only, such as when starting at a low energy and incrementally stepping up the pacing energy until capture is obtained, or presumed to be at least partially anodal, such as when starting at a high energy and incrementally decreasing the pacing energy; in either case, a deviation from the reference value can indicate a deviation from the presumption.

At 1406, the pacing energy can be incrementally changed, such as by stepping the pacing energy up or down incrementally, similar to that described above with respect to 706, but using the pace-to-activation delay of the ER signal.

At 1408, the resulting measured pace-to-activation delay (or resulting combined measured pace-to-activation delay) can be compared to one or more criteria, similar to that described above with respect to 708, although different criteria can be experimentally or otherwise determined and used here.

In an illustrative example, if at 1408 the measured pace-to-activation delay falls below a specified percentage (e.g., 80%) of the reference pace-to-activation delay, while incrementally stepping up pacing energy, then at 1410, onset of at least partial anodal capture can be declared, and at 1414, the example 1400 can be exited. Otherwise, at 1412, there is a return to 1406, and the pacing energy can be incrementally changed again, while monitoring the resulting ER signal to measure the resulting pace-to-activation delay, as described above with respect to FIG. 13. In an illustrative example, if at 1408 the measured pace-to-activation delay increases above a specified amount (e.g., 120%) of the reference pace-to-activation delay, while incrementally stepping down pacing energy, then at 1410, loss of at least partial anodal capture can be declared, and at 1414, the example 1400 can be exited.

Example F

The examples described can be used to detect a change in capture, such as by sensing a change in a time delay, Δt, between a pace and an ER feature, or by sensing a change in slope, ΔS, of a designated portion of the ER signal. In the example in which the change in capture is detected by sensing a change in time delay, the below Tables 1-3 can help explain how the change in time delay can be used to interpret the type of change in capture that has occurred. This can include using various sensing electrode configurations, such as:

1. Using a sensing electrode that is closer to an anode pacing electrode than to a cathode pacing electrode (see Table 1);

2. Using a sensing electrode that is closer to a cathode pacing electrode than to an anode pacing electrode (see Table 2); and 3. Using a sensing electrode that is approximately equidistant from an anode pacing electrode and a cathode pacing electrode (see Table 3).

The present techniques can be used to discriminate between different changes in capture type, where the capture type can include:

A. Intrinsic (no capture);

B. Cathodal-Only (without accompanying anodal capture);

C. Anodal-Only (without accompanying cathodal capture); and

D. Both (anodal and cathodal capture both present).

Further, a change in capture can, in certain circumstances, be distinguished from one or more other changes in capture, such as by comparing the changes in time delay associated with the different changes in capture, such as described below in Tables 1-3.

TABLE 1

Using sensing electrode closer to anode than to cathode

| Change in Capture? | Change of Time Delay Indicating The Change in Capture (Explanation) | Example of Applicable Sequence of Pacing Pulse Energies | Distinguishable from Other Changes in Capture? |
|---|---|---|---|
| a) Intrinsic → Cathodal Only | Decrease (intrinsic is slower than the paced activation for a sick heart) | Step-Up From Intrinsic | Can distinguish (a) from (b) or (c) since $\Delta t_a < \Delta t_b$ and $\Delta t_a < \Delta t_c$ |
| b) Intrinsic → Anodal Only | Decrease (intrinsic is slower than the paced activation for a sick heart) | Step-Up From Intrinsic | Can distinguish (b) from (a) since $\Delta t_a < \Delta t_b$ |
| c) Intrinsic → Both | Decrease (intrinsic is slower than the paced activation for a sick heart) | Step-Up From Intrinsic | Can distinguish (c) from (a) since $\Delta t_a < \Delta t_c$ |
| d) Cathodal Only → Intrinsic | Increase (intrinsic is slower than the paced activation for a sick heart) | Step-Down | Can distinguish (d) from (e) or (f) since $\Delta t_d > \Delta t_e$ and $\Delta t_d > \Delta t_f$ |
| e) Cathodal Only → Anodal Only | Decrease (anode is closer so see a decrease) | Constant pacing output with intermittent contact between electrodes and cardiac tissue | Can distinguish (d) from (e) since $\Delta t_d > \Delta t_e$ |
| f) Cathodal Only → Both | Decrease (anode is closer so see a decrease) | Step-Up | Can distinguish (d) from (f) since $\Delta t_d > \Delta t_f$ |
| g) Anodal Only → Intrinsic | Increase (intrinsic is slower than the paced activation for a sick heart) | Step-Down | Can distinguish (g) from (h) or (i) since $\Delta t_g > \Delta t_h$ and $\Delta t_g > \Delta t_i$ |
| h) Anodal Only → Cathodal Only | Increase (cathode is further away so see an increase) | Constant pacing output with intermittent contact between electrodes and cardiac tissue | Can distinguish (h) from (g) or (i) since $\Delta t_g > \Delta t_h$ and $\Delta t_h > \Delta t_i$ |
| i) Anodal Only → Both | No change in time delay can indicate this change in capture, since time delay is not expected to change for this change in capture | Step-Up | Can distinguish (i) from (g) or (h) since $\Delta t_g > \Delta t_i$ and $\Delta t_h > \Delta t_i$ |
| j) Both → Intrinsic | Increase (intrinsic is slower than the paced activation for a sick heart) | Step-Down | Can distinguish (j) from (k) or (l) since $\Delta t_j > \Delta t_k$ and $\Delta t_j > \Delta t_l$ |
| k) Both → Cathodal Only | Increase (cathode is further away so see an increase) | Step-Down | Can distinguish (k) from (j) or (l) since $\Delta t_j > \Delta t_k$ and $\Delta t_k > \Delta t_l$ |
| l) Both → Anodal Only | No change in time delay can indicate this change in capture, since time delay is not expected to change for this change in capture | Step-Down | Can distinguish (l) from (j) or (k) since $\Delta t_j > \Delta t_l$ and $\Delta t_k > \Delta t_l$ |

TABLE 2

Using sensing electrode closer to cathode than to anode

| Change in Capture? | Change of Time Delay Indicating The Change in Capture (Explanation) | Example of Applicable Sequence of Pacing Pulse Energies | Distinguishable from Other Changes in Capture? |
|---|---|---|---|
| a) Intrinsic → Cathodal Only | Decrease (intrinsic is slower than the paced activation for a sick heart) | Step-Up From Intrinsic | Can distinguish (a) from (b) since $\Delta t_b < \Delta t_a$ |
| b) Intrinsic → Anodal Only | Decrease (intrinsic is slower than the paced activation for a sick heart) | Step-Up From Intrinsic | Can distinguish from (a) and (c) since $\Delta t_b < \Delta t_a$ and $\Delta t_b < \Delta t_c$ |
| c) Intrinsic → Both | Decrease (intrinsic is slower than the paced activation for a sick heart) | Step-Up From Intrinsic | Can distinguish from (b) since $\Delta t_b < \Delta t_c$ |
| d) Cathodal Only → Intrinsic | Increase (intrinsic is slower than the paced activation for a sick heart) | Step-Down | Can distinguish (d) from (e) or (f) since $\Delta t_d > \Delta t_e$ and $\Delta t_d > \Delta t_f$ |
| e) Cathodal Only → Anodal Only | Increase (anode is farther so see an increase) | Constant pacing output with intermittent contact between electrodes and cardiac tissue | Can distinguish (e) from (d) and (f) since $\Delta t_d > \Delta t_e$ and since $\Delta t_e > \Delta t_f$ |
| f) Cathodal Only → Both | No change in time delay can indicate this change in capture, since time delay is not expected to change for this change in capture | Step-Up | Can distinguish (f) from (d) and (e) since $\Delta t_d > \Delta t_f$ and since $\Delta t_e > \Delta t_f$ |
| g) Anodal Only → Intrinsic | Increase (intrinsic is slower than the paced activation for a sick heart) | Step-Down | Can distinguish (g) from (h) or (i) since $\Delta t_g > \Delta t_h$ and $\Delta t_g > \Delta t_i$ |
| h) Anodal Only → Cathodal Only | Decrease (cathode is closer so see a decrease) | Constant pacing output with intermittent contact between electrodes and cardiac tissue | Can distinguish (h) from (g) since $\Delta t_g > \Delta t_h$ |
| i) Anodal Only → Both | Decrease (cathode is closer so see a decrease) | Step-Up | Can distinguish (i) from (g) since $\Delta t_g > \Delta t_i$ |
| j) Both → Intrinsic | Increase (intrinsic is slower than the paced activation for a sick heart) | Step-Down | Can distinguish (j) from (k) and (l) since $\Delta t_j > \Delta t_k$ and since $\Delta t_j > \Delta t_l$ |
| k) Both → Cathodal Only | No change in time delay can indicate this change in capture, since time delay is not expected to change for this change in capture | Step-Down | Can distinguish (k) from (j) and (l) since $\Delta t_j > \Delta t_k$ and $\Delta t_l > \Delta t_k$ |
| l) Both → Anodal Only | Increase (anode is farther away, so see an increase) | Step-Down | Can distinguish (l) from (j) and (k) since $\Delta t_j > \Delta t_l$ and $\Delta t_l > \Delta t_k$ |

TABLE 3

Using sensing electrode about equidistant to cathode and anode

| Change in Capture? | Change of Time Delay Indicating The Change in Capture (Explanation) | Example of Applicable Sequence of Pacing Pulse Energies | Distinguishable from Other Changes in Capture? |
|---|---|---|---|
| a) Intrinsic → Cathodal Only | Decrease (intrinsic is slower than the paced activation for a sick heart) | Step-Up From Intrinsic | |
| b) Intrinsic → Anodal Only | Decrease (intrinsic is slower than the paced activation for a sick heart) | Step-Up From Intrinsic | |
| c) Intrinsic → Both | Decrease | Step-Up From Intrinsic | |
| d) Cathodal Only → Intrinsic | Increase (intrinsic is slower than the paced activation for a sick heart) | Step-Down | Can distinguish (d) from (e) or (f) since $\Delta t_d > \Delta t_e$ and $\Delta t_d > \Delta t_f$ |
| e) Cathodal Only → Anodal Only | No change in time delay can indicate this change in capture, since time delay is not expected to change for this change in capture | Constant pacing output with intermittent contact between electrodes and cardiac tissue | Can distinguish (e) from (d) since $\Delta t_d > \Delta t_e$ |
| f) Cathodal Only → Both | No change in time delay can indicate this change in capture, since time delay is not expected to change for this change in capture | Step-Up | Can distinguish (f) from (d) since $\Delta t_d > \Delta t_f$ |
| g) Anodal Only → Intrinsic | Increase (intrinsic is slower than the paced activation for a sick heart) | Step-Down | Can distinguish (g) from (h) or (i) since $\Delta t_g > \Delta t_h$ and $\Delta t_g > \Delta t_i$ |
| h) Anodal Only → Cathodal Only | No change in time delay can indicate this change in capture, since time delay is not expected to change for this change in capture | Constant pacing output with intermittent contact between electrodes and cardiac tissue | Can distinguish (h) from (g) since $\Delta t_g > \Delta t_h$ |
| i) Anodal Only → Both | No change in time delay can indicate this change in capture, since time delay is not expected to change for this change in capture | Step-Up | Can distinguish (i) from (g) since $\Delta t_g > \Delta t_i$ |
| j) Both → Intrinsic | Increase (intrinsic is slower than the paced activation for a sick heart) | Step-Down | Can distinguish (j) from (k) and (l) since $\Delta t_j > \Delta t_k$ and since $\Delta t_j > \Delta t_l$ |
| k) Both → Cathodal Only | No change in time delay can indicate this change in capture, since time delay is not expected to change for this change in capture | Step-Down | Can distinguish (k) from (j) since $\Delta t_j > \Delta t_k$ |
| l) Both → Anodal Only | No change in time delay can indicate this change in capture, since time delay is not expected to change for this change in capture | Step-Down | Can distinguish (l) from (j) since $\Delta t_j > \Delta t_l$ |

Example G

The example of the cardiac function management of FIG. 1 can include a circuit to monitor the performance of the hemodynamic system of the subject. Hemodynamic monitoring can provide a check on the efficacy of the anodal stimulation. Heart-sounds are useful indications of proper functioning or improper functioning of a patient's heart and can provide an indication of hemodynamic performance. A heart-sound is associated with mechanical vibrations from activity of a patient's heart and the flow of blood through the heart. Heart-sounds recur with each cardiac cycle and are separated and classified according to the activity associated with the vibration. The first heart-sound (S1) is the vibrational sound made by the heart during tensing of the mitral valve. The second heart-sound (S2) marks the beginning of diastole. The third heart-sound (S3) and fourth heart-sound (S4) are related to filling pressures of the left ventricle during diastole. Presence of S3 and S4 is typically abnormal.

The implantable device 102 of FIG. 1 can include a heart-sound sensing circuit that senses a heart-sound signal representative of mechanical activation of the heart of the subject. As explained previously, the activity sensor 113 of FIG. 1 can include an accelerometer that can sense heart-sounds. The controller circuit 116 may monitor a parameter of at least one heart-sound detected in the heart-sound signal. A non-exhaustive list of heart-sound parameters includes the amplitude of the S1 or S2 heart-sound, the time duration of the S1 or S2 heart-sound, and the amplitude or even the presence of an S3 or S4 heart-sound.

A heart-sound can be identified in a heart-sound signal by the controller circuit 116 in a variety of ways. In certain examples, a heart-sound is identified using a morphology analysis of the heart-sound signal. In certain examples, a heart-sound is identified by a time relationship from a fiducial (e.g., an R-wave peak) identified in a sensed cardiac signal.

The controller circuit 116 adjusts the electrostimulation energy while monitoring a characteristic of the ER signal until detecting at least partial anodal capture. The controller circuit 116 may monitor the heart-sound parameter after at least partial anodal capture is detected or monitor the heart-sound parameter both before and after the at least partial anodal capture is detected. When the monitored heart-sound parameter indicates that the hemodynamic performance of the patient is maintained or improved, the controller circuit 116 adopts the electrostimulation adjustment. The adjustment may include one or more parameters related to electrostimulation magnitude (e.g., amplitude), duration (e.g., pulse width), or an electrode configuration used to deliver the stimulus. When the monitored heart-sound parameter indicates that the hemodynamic performance of the patient has decreased, the controller circuit 116 may reject the electrostimulation adjustment. Rejecting the electrostimulation adjustment may include altering therapy settings to end the anodal stimulation, such as by changing the electrostimulation or arrangement of electrodes used to deliver the electrostimulation.

Example H

Figure 15:
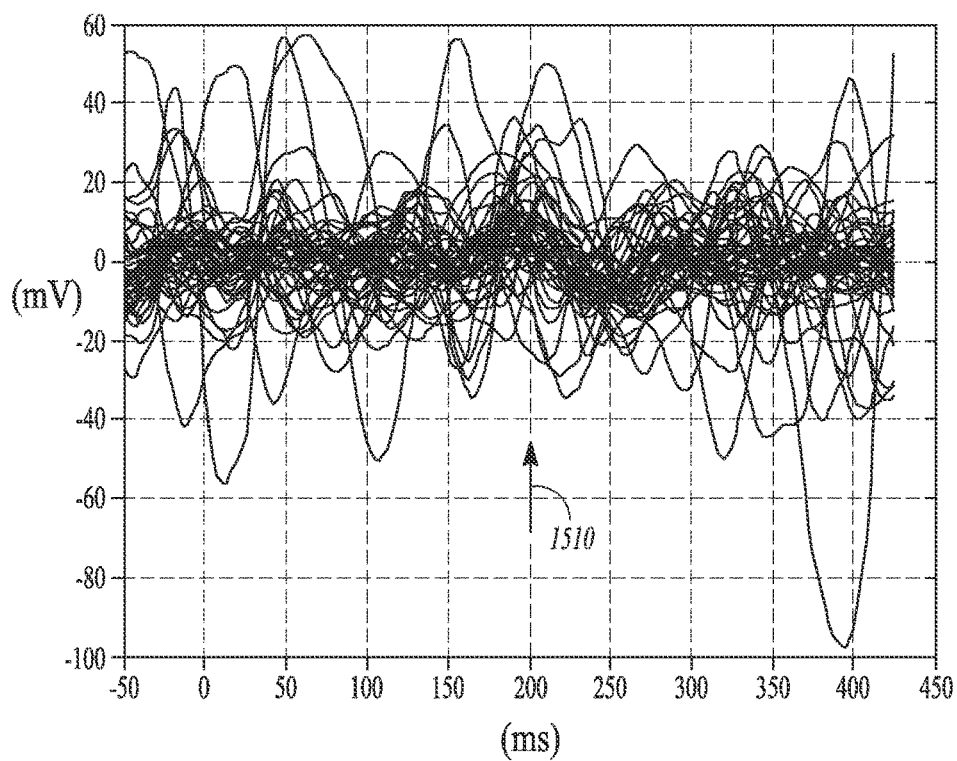
FIG. 15 is an amplitude vs. time graph of showing multiple tracings of heart-sound signals resulting from cathodal-only capture.

A heart-sound signal can also be used as an ER signal. FIG. 15 is an amplitude vs. time graph showing multiple tracings of heart-sound signals resulting from cathode-only capture that occurs at time zero milliseconds (t=0 ms). The arrow 1510 indicates the approximate time of the S1 heart-sound at t=200 ms. Electrostimulation at t=0 was provided using an LV ring electrode and an LV tip electrode.

Figure 16:
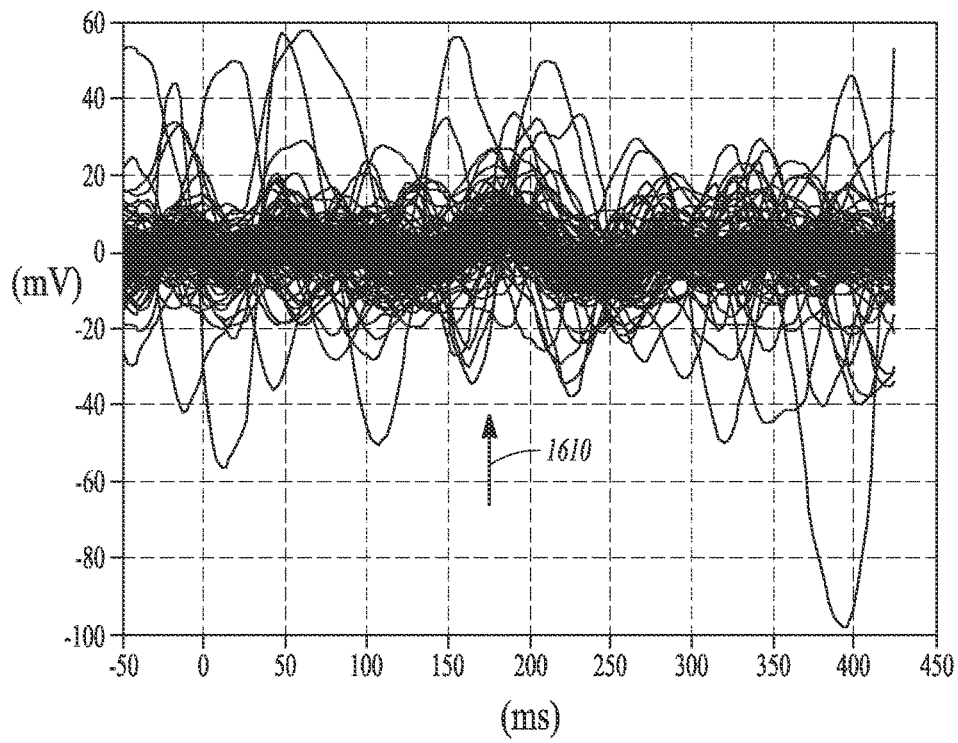
FIG. 16 is an amplitude vs. time graph showing multiple tracings of (1) cathodal-only capture heart-sound signals and (2) combined anodal and cathodal heart-sound signals.

FIG. 16 is an amplitude vs. time graph showing multiple tracings of heart-sound signals resulting from combined anode and cathode capture overlaid onto the tracings of FIG. 15. Electrostimulation again corresponds to t=0. The arrow 1610 indicates the approximate time of the S1 heart-sound. It can be seen from the Figure that the S1 heart-sound occurs earlier, at about t=175 ms, than the cathode-only case. The data shows that a shift in time delay from the time of electrostimulation to the time of the S1 heart-sound can be used to discriminate between cathode-only capture and combined anodal and cathodal capture. Thus, a change in capture may be adopted when a heart-sound signal indicates that the change is beneficial.

Figure 17:
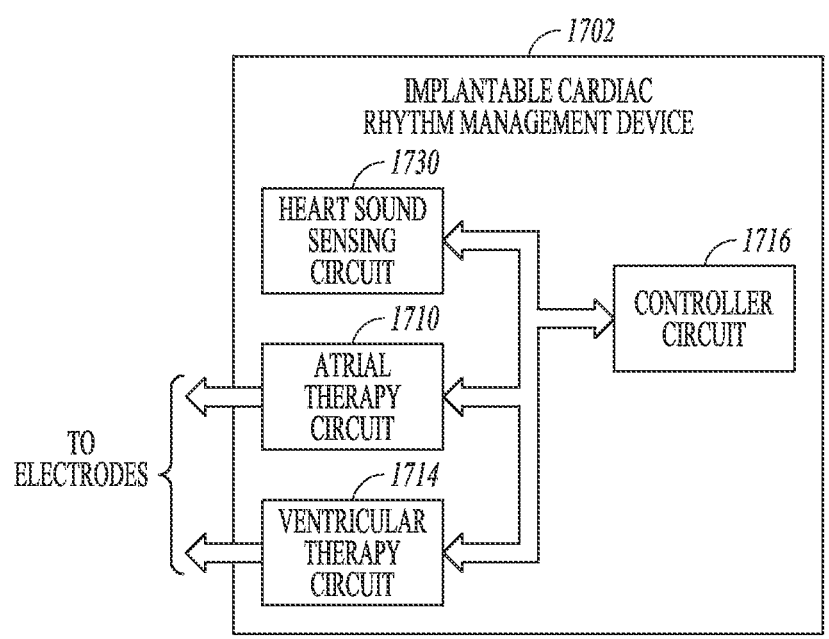
FIG. 17 shows an example of portions of an implantable medical device.

FIG. 17 shows another example of portions of an implantable cardiac rhythm management device 1702. The device 1702 includes an electrostimulation energy delivery circuit such as one or both of an atrial therapy circuit 1710 and a ventricular therapy circuit 1712. The electrostimulation energy delivery circuit issues electrostimulations using first and second pacing electrodes.

The device 1702 also includes a heart-sound sensing circuit 1730 that senses an ER signal as a heart-sound signal representative of mechanical activation of the heart of the subject. Some examples of a heart-sound sensing circuit 1730 include one or more of an accelerometer, a microphone, and a strain gauge. The heat sound sensing circuit 1730 senses the ER or heart-sound signal in response to an electrostimulation. The sensed ER signal can include one or more of an S1, S2, S3, and S4 heart-sounds.

The device 1702 also includes a controller circuit 1716 electrically coupled to the heart-sound sensing circuit and the electrostimulation energy-delivery circuit. The controller circuit 1716 adjusts electrostimulation energy while monitoring a characteristic of the ER signal and is capable of distinguishing a change in at least partially anodal capture. The controller circuit 1716 declares a change in capture when the characteristic of the ER signal meets at least one criterion.

The characteristic can include a time delay in the ER signal between an electrostimulation and a feature of a heart-sound responsive to the electrostimulation. In certain examples, the characteristic can be a time delay between the electrostimulation and an onset of a heart-sound (e.g., the onset of the S1, S2, S3, or S4 heart-sound). In certain examples, the characteristic can be a time delay between the electrostimulation and a peak (e.g., peak amplitude) of a heart-sound in the ER signal. In certain examples, the characteristic can be an appearance of a heart-sound (e.g., one or more of the S3 and S4 heart-sounds) in the ER signal.

The controller circuit 1716 may declare that the criterion is met when the time delay satisfies a specified (e.g., programmed) time delay threshold. The criterion can be selected to identify a change in the time delay that corresponds to a shift from cathodal-only capture to at least partially anodal capture (e.g., a decrease of 25 ms in the time delay in FIG. 15 of the S1 heart-sound). Conversely, the criterion can be selected to identify a shift from at least partially anodal capture to cathodal-only capture (e.g., an increase of 25 ms in the time delay in FIG. 15 of the S1 heart-sound). In some examples, the criterion can be met when the amplitude of a heart-sound feature satisfies a specified amplitude threshold.

The electrostimulation can be within-chamber, such as by issuing electrostimulation to a first LV electrode (e.g., electrode 320A in FIG. 3) and a second LV electrode (e.g., electrode 320D in FIG. 3). The electrostimulation can be cross-chamber, such as by issuing electrostimulation to a first LV electrode (e.g., one or more of electrodes 212, 214 in FIG. 2) and an RV electrode (e.g., electrode 208 in FIG. 2).

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus for electrical coupling to a plurality f implantable electrodes, the apparatus comprising:
   an electrostimulation energy delivery circuit configured to issue electrostimulations to the plurality of electrodes;
   an evoked response (ER) sensing circuit configured to sense an ER signal using the plurality of electrodes; and
   a controller circuit to selectively configure a stimulation vector that includes a first electrode for either one of an anode or a cathode of the stimulation vector and a plurality of other electrodes as a second combined electrode for the other of the anode or the cathode of the stimulation vector, wherein the controller circuit is programmed to:
   adjust the electrostimulation energy to deliver anodal stimulation using one of the first electrode or the second combined electrode as the anode; and
   detect anodal capture at the first electrode or the second combined electrode when monitoring a characteristic of the sensed ER signal.

2. The apparatus of claim 1, including the first electrode and the second combined electrode, wherein the first electrode is configured for placement in a right ventricle (RV) and the second combined electrode is configured for placement in the left ventricle (LV), and wherein the controller circuit is configured to adjust the electrostimulation to deliver RV anodal stimulation using the first electrode and LV cathodal stimulation using the electrodes of the second combined electrode.

3. The apparatus of claim 1, including the first electrode and the second combined electrode, wherein the first electrode is configured for placement in the RV and the second combined electrode is configured for placement in the LV, and wherein the controller circuit is configured to adjust the electrical stimulation to deliver RV anodal stimulation using the first electrode simultaneously with LV cathodal stimulation using at least one electrode of the second combined vector electrode.

4. The apparatus of claim 1, including the first electrode and the second combined electrode, wherein the first electrode is configured for placement in the LV and the second combined electrode is configured for placement in the LV, and wherein the controller circuit is configured to adjust the electrical stimulation to an anodal capture mode that delivers LV anodal stimulation using the first electrode and LV cathodal stimulation using the electrodes of the second combined vector electrode.

5. The apparatus of claim 4, wherein the controller circuit is configured to adjust the electrostimulation to deliver the LV anodal stimulation using the first electrode simultaneously LV cathodal stimulation using the electrodes of the second combined electrode.

6. The apparatus of claim 1, wherein the first electrode is combined with at least one other electrode to form a first combined electrode, wherein the controller circuit is configured to adjust the electrostimulation to deliver anodal stimulation using the first combined electrode and to deliver cathodal stimulation using the second combined electrode.

7. The apparatus of claim 1, the second combined electrode is configured as a pacing cathode.

8. The apparatus of claim 1, wherein the controller circuit is configured to indicate a change in anodal capture including a shift from cathodal-only capture to at least partially anodal capture and indicate a shift from at least partially anodal capture to cathodal-only capture, when the characteristic of the ER signal meets at least one criteria.

9. The apparatus of claim 8, wherein the ER sensing circuit includes a heart-sound sensing circuit and is configured to sense the ER signal as a heart-sound signal representative of mechanical activation of the heart of the subject.

10. The apparatus of claim 1, including a heart-sound sensing circuit configured to sense a heart-sound signal representative of mechanical activation of the heart of the subject, and wherein the controller circuit is configured to monitor a heart sound parameter using the heart sound signal and adopt the anodal stimulation according to the monitored heart sound parameter.

11. A method of controlling operation of a medical device, the method comprising:
   selectively configuring a stimulation vector that includes a first electrode for either one of an anode or a cathode of the stimulation vector and a plurality of other electrodes as a second combined electrode for the other of the anode or the cathode of the stimulation vector;
   issuing electrostimulations to the stimulation vector;
   sensing an evoked response (ER) signal and monitoring a characteristic of the sensed ER signal;
   adjusting the electrostimulation energy to deliver anodal stimulation using the first electrode or the second combined electrode; and
   detecting anodal capture from the anodal stimulation according to the characteristic of the sensed ER signal.

12. The method of claim 11, wherein adjusting the electrostimulation energy includes adjusting the electrostimulation energy to an anodal capture mode that delivers right ventricle (RV) anodal stimulation using the first electrode and LV cathodal stimulation using the electrodes of the second combined electrode.

13. The method of claim 11, wherein adjusting the electrostimulation energy includes adjusting the electrostimulation energy to deliver RV anodal stimulation using the first electrode simultaneously with LV cathodal stimulation using at least one electrode of the second combined electrode.

14. The method of claim 11, wherein adjusting the electrostimulation energy includes adjusting the electrostimulation energy to deliver LV anodal stimulation using the first electrode and LV cathodal stimulation using the electrodes of the second combined electrode.

15. The method of claim 11, wherein detecting anodal capture includes detecting, when the characteristic of the ER signal meets at least one criteria, a shift from cathodal-only capture to at least partially anodal capture and detecting a shift from at least partially anodal capture to cathodal-only capture.

16. The apparatus of claim 11, wherein sensing an ER signal includes sensing a heart-sound signal representative of mechanical activation of the heart of the subject and monitoring a characteristic of the sensed heart-sound signal, and wherein detecting anodal capture includes detecting anodal capture from the anodal stimulation according to the monitored characteristic of the sensed heart-sound signal.

17. The apparatus of claim 11, including monitoring a heart sound parameter using the heart sound signal and adopting the anodal stimulation according to the monitored heart sound parameter.

18. An apparatus comprising:
a first cardiac lead including at least one lead electrode;
a second cardiac lead including a plurality of lead electrodes;
an electrostimulation energy delivery circuit configured to issue electrostimulations to the lead electrodes of the first and second cardiac leads;
an evoked response (ER) sensing circuit configured to sense an ER signal using the lead electrodes of the first and second cardiac leads; and
a controller circuit to configure a stimulation vector that includes a first electrode of the first cardiac lead for one of an anode or a cathode of the stimulation vector and a plurality of other electrodes of the second cardiac lead as a second combined electrode for the other of the anode or the cathode of the stimulation vector, wherein the controller circuit is configured to:
adjust the electrostimulation energy to deliver anodal stimulation using the first electrode or the second combined electrode as the anode; and
detect anodal capture at the first electrode or the second combined electrode by monitoring a characteristic of the sensed ER signal.

19. The apparatus of claim 18, wherein the first electrode is configured for placement in a right ventricle (RV) and the second combined electrode is configured for placement in the left ventricle (W), and wherein the controller circuit is configured to adjust the electrostimulation to deliver RV anodal stimulation using the first electrode and LV cathodal stimulation using the electrodes of the second combined electrode.

20. The apparatus of claim 18, including a heart-sound sensing circuit configured to sense a heart-sound signal representative of mechanical activation of the heart of the subject, and wherein the controller circuit is configured to monitor a heart sound parameter using the heart sound signal and adopt the anodal stimulation according to the monitored heart sound parameter.

* * * * *